United States Patent
Bates et al.

(10) Patent No.: US 8,592,563 B2
(45) Date of Patent: Nov. 26, 2013

(54) ANTIBODIES SPECIFIC TO PRO-ANGIOGENIC ISOFORMS OF VASCULAR ENDOTHELIAL GROWTH FACTOR (VEGF)

(75) Inventors: David O. Bates, Bishopston Bristol (GB); Steven J. Harper, Tintern Gwent (GB); Miriam Y. Mengelus, Holon (IL); Menachem Ze'evi, Ramat Gan (IL)

(73) Assignees: Philogene, Inc., Summit, NJ (US); University of Bristol, Bristol (GB)

( * ) Notice: Subject to any disclaimer, the term of this patent is extended or adjusted under 35 U.S.C. 154(b) by 0 days.

(21) Appl. No.: 12/739,619

(22) PCT Filed: Oct. 26, 2008

(86) PCT No.: PCT/IL2008/001410
§ 371 (c)(1),
(2), (4) Date: Jul. 12, 2010

(87) PCT Pub. No.: WO2009/053987
PCT Pub. Date: Apr. 30, 2009

(65) Prior Publication Data
US 2010/0272733 A1    Oct. 28, 2010

Related U.S. Application Data

(60) Provisional application No. 60/982,438, filed on Oct. 25, 2007.

(51) Int. Cl.
*C07K 16/00* (2006.01)
*C07K 16/22* (2006.01)

(52) U.S. Cl.
USPC .................. 530/388.1; 530/387.1; 530/388.23

(58) Field of Classification Search
None
See application file for complete search history.

(56) References Cited

U.S. PATENT DOCUMENTS

| | | | |
|---|---|---|---|
| 5,530,101 A * | 6/1996 | Queen et al. | 530/387.3 |
| 6,022,541 A * | 2/2000 | Senger et al. | 424/172.1 |
| 2005/0054036 A1* | 3/2005 | Bates et al. | 435/69.1 |
| 2006/0286636 A1* | 12/2006 | Shima et al. | 435/69.1 |
| 2008/0031815 A1* | 2/2008 | Chen et al. | 424/9.1 |

FOREIGN PATENT DOCUMENTS

| | | | |
|---|---|---|---|
| WO | WO 98/39037 | * | 9/1998 |
| WO | WO-98/39037 A1 | | 9/1998 |
| WO | WO-03/012105 A2 | | 2/2003 |
| WO | WO-2005/007198 A2 | | 1/2005 |
| WO | WO-2005/054273 A2 | | 6/2005 |
| WO | WO-2008/110777 A2 | | 9/2008 |

OTHER PUBLICATIONS

Yu et al, Investigative Ophthalmology & Visual Science 49(2): 522-527, Feb. 2008.*
Colman et al, in Research in Immunology, 145(1):33-36, 1994.*
Lederman et al, in Molecular Immunology, 28:1171-1181, 1991.*
Stancovski et al, Proceedings of the National Academy of Science USA 88: 8691-8695, 1991.*
Riemer et al, Mol. Immunol. 42: 1121-1124, 2005.*
Perrin et al, Diabetologia 48: 2422-2427, 2005.*
Woolard, J. et al., "VEGF$_{165}$b, an Inhibitory Vasular Endothelial Growth Factor Splice Variant: Mechanism of Action, In vivo Effect on Angiogenesis and Endogenous Protein Expression" Cancer Res, 64:7822-7835 (2004).
Perrin, R.M. et al., "Diabetic retinopathy is associated with a switch in splicing from anti- to pro-angiogenic isoforms of vascular endothelial growh factor Diabetologica", 48:(11):2422-2427 (2005).
Pritchard-Jones, R.O. et al., "Expression of VEGF$_{xxx}$b, the inhibitory isoforms of VEGF, in malignant melanoma" British Journal of Cancer, 97:(2):223-230 (2007).
Konopatskaya, O. et al., "VEGF$_{165}$b, an endogenous C-terminal splice variant of VEGF, inhibits retinal neovascularization in mice" Molecular Vision, 12:(67-69):626-632 (2006).
For the European Orgranisation for Research and Treatment of Cancer et al., "Phase I investigation of recombinant anti-human vascular endothelial growth factor antibody in patients with advanced cancer" European Journal of Cancer, 41:(4):555-563 (2005).
Zhang, W. et al., "A monoclonal antibody that blocks VEGF binding to VEGFR2 (KDR/Flk-1) inhibits vascular expression of Flk-1 and tumor growth in an orthotopic human breast cancer model" Angiogenesis, 5:(1-2):35-44 (2002).

* cited by examiner

*Primary Examiner* — Phuong Huynh
(74) *Attorney, Agent, or Firm* — Choate, Hall & Stewart LLP; Fangli Chen; Rolando Medina

(57) ABSTRACT

The present invention provides antibodies, as well as molecules having at least the antigen-binding portion of an antibody, against agonist pro-angiogenic, pro-permeability, vasodilatory isoforms of VEGF. Disclosed antibodies and antibody fragments are characterized by being capable of binding to and neutralizing pro-angiogenic forms of VEGF while not effecting isoforms of VEGF which are anti angiogenic. Methods of production and use in therapy and diagnosis, of such antibodies and antibody fragments are also provided.

4 Claims, 10 Drawing Sheets

SEQUENCE LISTING

<160> NUMBER OF SEQ ID NOS: 7

<210> SEQ ID NO 1
<211> LENGTH: 6
<212> TYPE: PRT
<213> ORGANISM: Homo sapiens

<400> SEQUENCE: 1

Cys Asp Lys Pro Arg Arg
1               5

<210> SEQ ID NO 2
<211> LENGTH: 6

-continued

```
<212> TYPE: PRT
<213> ORGANISM: Homo sapiens

<400> SEQUENCE: 2

Ser Leu Thr Arg Lys Asp
1               5

<210> SEQ ID NO 3
<211> LENGTH: 7
<212> TYPE: PRT
<213> ORGANISM: Homo sapiens

<400> SEQUENCE: 3

Arg Cys Asp Lys Pro Arg Arg
1               5

<210> SEQ ID NO 4
<211> LENGTH: 8
<212> TYPE: PRT
<213> ORGANISM: Homo sapiens

<400> SEQUENCE: 4

Cys Arg Cys Asp Lys Pro Arg Arg
1               5

<210> SEQ ID NO 5
<211> LENGTH: 9
<212> TYPE: PRT
<213> ORGANISM: Homo sapiens

<400> SEQUENCE: 5

Thr Cys Arg Cys Asp Lys Pro Arg Arg
1               5

<210> SEQ ID NO 6
<211> LENGTH: 12
<212> TYPE: PRT
<213> ORGANISM: Homo sapiens

<400> SEQUENCE: 6

Asp Arg Ala Arg Gln Glu Cys Asp Lys Pro Arg Arg
1               5                   10

<210> SEQ ID NO 7
<211> LENGTH: 7
<212> TYPE: PRT
<213> ORGANISM: Homo sapiens

<400> SEQUENCE: 7

Asp Arg Ala Arg Gln Glu Lys
1               5
```

US 8,592,563 B2

ANTIBODIES SPECIFIC TO PRO-ANGIOGENIC ISOFORMS OF VASCULAR ENDOTHELIAL GROWTH FACTOR (VEGF)

REFERENCE TO RELATED APPLICATIONS

This application is a national phase application of International Application No. PCT/IL2008/001410 (PCT Pub. No. WO/2009/053987), filed Oct. 26, 2008, which claims priority to U.S. Provisional Application No. 60/982,438, filed Oct. 25, 2007, the entire contents of both of which are incorporated herein by reference.

SEQUENCE LISTING

In accordance with 37 CFR 1.52(e)(5), a Sequence Listing in the form of a text file (entitled "SequenceListing.txt," created on Apr. 13, 2010, and 2 kilobytes in size) is incorporated herein by reference in its entirety.

FIELD OF THE INVENTION

The present invention relates to therapeutic and diagnostic antibodies, useful in the treatment of diseases involving angiogenesis including tumors and retinal disorders. In particular the present invention provides antibodies specific to pro angiogenic isoforms of VEGF.

BACKGROUND OF THE INVENTION

Angiogenesis

Angiogenesis is an important cellular event in which vascular endothelial cells proliferate, prune and reorganize to form new vessels from preexisting vascular networks. There is compelling evidence that the development of a vascular supply is essential for normal and pathological proliferative processes (Folkman and Klagsbrun 1987, Science 235, 442-447). Delivery of oxygen and nutrients, as well as the removal of catabolic products, represent rate-limiting steps in the majority of growth processes occurring in multicellular organisms. Thus, the vascular compartment is necessary not only for organ development and differentiation during embryogenesis, but also for wound healing and reproductive functions in the adult.

Angiogenesis is also implicated in the pathogenesis of a variety of disorders, including but not limited to, tumors, proliferative retinopathies, age-related macular degeneration, rheumatoid arthritis, and psoriasis. Angiogenesis is essential for the growth of most primary tumors and their subsequent metastasis. Tumors can absorb sufficient nutrients and oxygen by simple diffusion up to a size of 1-2 mm, at which point their further growth requires the elaboration of a vascular supply. This process is thought to involve recruitment of the neighboring host mature vasculature to begin sprouting new blood vessel capillaries, which grow towards, and subsequently infiltrate, the tumor mass. In addition, tumor angiogenesis involves the recruitment of circulating endothelial precursor cells from the bone marrow to promote neovascularization (Kerbel 2000, Carcinogenesis, 21, 505-515; Lynden et al., 2001, Nat. Med. 7, 1194-1201)

In view of the remarkable physiological and pathological importance of angiogenesis, much work has been dedicated to the elucidation of the factors capable of regulating this process. It is suggested that the angiogenesis process is regulated by a balance between pro- and anti-angiogenic molecules, and is derailed in various diseases, especially cancer (Carmeliet and Jain 2000, Nature 407, 249-257).

Vascular Endothelial Growth Factor (VEGF)

Vascular endothelial cell growth factor (VEGF), the most prevalent form which is VEGF-A or vascular permeability factor (VPF), has been reported as a pivotal regulator of both normal and abnormal angiogenesis (Ferrara and Davis-Smyth, 1997, Endocrine Rev. 18, 4-25). Compared to other growth factors that contribute to the processes of vascular formation, VEGF is unique in its high specificity for endothelial cells within the vascular system. VEGF is essential for embryonic vasculogenesis and angiogenesis (Carmeliet et al., 1996, Nature 380, 435-439; Ferrara et al., 1996, Nature 380, 439-442). Furthermore, VEGF is required for the cyclical blood vessel proliferation in the female reproductive tract and for bone growth and cartilage formation (Ferrara et al. 1998, Nature Med. 4, 336-340; Gerber et al., 1999, Nature Med., 5, 623-628). Human VEGF is a 32-42 kDa dimeric glycoprotein that mediates vasodilatation, increased vascular permeability and endothelial cell mitogenesis.

Substantial evidence also implicates VEGF's critical role in the development of conditions or diseases that involve pathological angiogenesis. The VEGF mRNA is overexpressed by the majority of human tumors examined. Given its central role in promoting tumor growth, VEGF provides an attractive target for therapeutic intervention. Indeed, a variety of therapeutic strategies aimed at blocking VEGF or its receptor signaling system are currently being developed for the treatment of neoplastic diseases. So far, VEGF/VEGF receptor blockade by monoclonal antibodies and inhibition of receptor signaling by tyrosine kinase inhibitors are the best studied and clinically accepted approaches. VEGFR-1 ribozymes, VEGF toxin conjugates, and soluble VEGF receptors are also being investigated.

A number of different strategies to inhibit VEGF signal transduction are in therapeutic use or in development and they include humanized neutralizing monoclonal antibodies, soluble receptors, antagonistic VEGF mutants and peptides, and inhibitors of VEGF receptor function. A review of VEGF inhibition was recently published by Moreira et al. (Anti-Cancer Agents in Medicinal Chemistry 2007, 7, 223-245).

Differential exon splicing of the VEGF gene results in 2 families of isoforms: the first family has been termed stimulatory, agonist or pro-angiogenic and the second has become known as the inhibitory, antagonistic or anti-angiogenic family. These two families are very similar structurally but distinct functionally. There are three main mRNA species which code for five agonist secreted isoforms denoted $VEGF_{206}$, $VEGF_{189}$, $VEGF_{165}$, $VEGF_{145}$ and $VEGF_{121}$. Thus, the pro-angiogenic VEGF family has five different forms having 121, 145, 165, 189 and 206 amino acids due to alternative splicing. $VEGF_{121}$ $VEGF_{145}$ and $VEGF_{165}$ are soluble and are capable of promoting angiogenesis, whereas $VEGF_{189}$ and $VEGF_{206}$ are bound to heparin containing proteoglycans at the cell surface. A number of minor splice variants have been described but their importance remains uncertain. Each isoform has distinct properties and patterns of expression. Various molecular forms of VEGF are disclosed in WO 03/012105 and share a common amino-terminal domain consisting of 110 amino acids of Exons 1 to 5, but differ in the length of the carboxyl-terminal portion (see FIG. 1).

The Anti-Angiogenic VEGF Isoforms

A family of VEGF splice variants (also designated herein as $VEGF_{xxx}b$) are anti-angiogenic isoforms of VEGF, including but not limited to $VEGF_{165}b$ $VEGF_{145}b$ $VEGF_{189}b$, $VEGF_{206}b$, (as disclosed in WO 03/012105), and $VEGF_{121}b$, that were identified by Bates and Harper. These variants are differentially spliced lacking exons 6 and 8a (previously termed exon 8) and comprising the previously unknown exon 8b (previously called exon 9) encoding the amino acid sequence Ser-Leu-Thr-Arg-Lys-Asp (SLTRKD, SEQ ID NO:2). The VEGF$_{165}$b, and other agonist VEGF species (also designated herein VEGF$_{xxx}$b), are antagonists of the conventional VEGF polypeptides and are have been shown by Bates and Harper to possess anti-angiogenic, anti-vasodilatory, anti-permeability and anti-proliferative activity (Woolard et al., Cancer Research 2002, 62, 4123-4131, and Cancer Research 2004, 64, 7822-7835). In a recent publication of Harper and Bates (Varey et al., British J. Cancer 2008, 1-14), the authors conclude that VEGF$_{165}$b inhibits colorectal tumor growth. Furthermore, VEGF$_{165}$b decreases the effect of Bevacizumab (AVASTIN®) on the tumor growth.

Soker et al. (J. Biol. Chem. 1997, 272, 50, 31582-31588) describes a peptide corresponding to the Exon 7-encoded domain of VEGF$_{165}$ which inhibits VEGF-induced endothelial cell proliferation.

WO 98/16551 relates, in general, to VEGF antagonists which are able to bind to and occupy VEGF receptors without inducing a native VEGF response. The VEGF variants have amino acid modifications that affect the ability of the VEGF monomeric units to properly dimerize. The variants specifically disclosed have at least one modified cysteine residue that inhibits the ability of the variant to dimerize through the formation of disulfide bonds.

WO 01/53345 relates to a method for treating or preventing a disease comprising formation of VEGF heterodimer and to novel VEGF isoforms capable of forming such a heterodimer.

WO 01/12809 discloses a VEGF antagonist which is a VEGF derived molecule having a mutation in its loop I like sequence which enables it to significantly reduce the activation of VEGF receptors in the presence of the wild type dimer.

WO 2005/000900 discloses method of treating cancer comprising administering to the patient effective amounts of an anti-VEGF antibody together with an anti-neoplastic composition containing a chemotherapeutic agent.

US 2006/166878 discloses a portion of the seventh exon of VEGF$_{165}$ claiming that this portion acts as an antagonist to all VEGF isoforms. The antibodies disclosed in US 2006/166878 bind both agonist as well as antagonist isoforms of VEGF.

Anti VEGF Antibodies

The anti-VEGF antibody "Bevacizumab (BV)", also known as "rhuMAb VEGF" or "AVASTIN®", is a recombinant humanized anti-VEGF monoclonal antibody generated according to Presta et al., 1997, Cancer Res., 57, 4593-4599. AVASTIN® is approved for therapeutic use and is further investigated clinically for treating various cancers.

AVASTIN® is directed against the Exon 3/Exon 4 junction sequence which is highly conserved in all VEGF isoforms whether agonistic or antagonistic.

WO 98/45331 discloses anti VEGF antibodies and their diagnostic and therapeutic uses while WO 98/45332 discloses human VEGF antibodies and methods for their production and use.

WO 2001/036972 discloses an ELISA method for detecting VEGF using monoclonal antibodies directed against different epitopes of VEGF. The described method enables detection of all isoforms of VEGF together in one assay.

WO 2005/054273 discloses methods for designing and selecting humanized or fully human antibodies against vascular endothelial growth factor (VEGF) with high affinity and specificity. In particular, humanized or human anti-VEGF monoclonal antibodies are provided with ability to bind to human VEGF with high affinity, inhibit VEGF-induced proliferation of endothelial cells in vitro and inhibit VEGF-induced angiogenesis in vivo. These antibodies and their derivative can be used in a wide variety of applications such as diagnosis, prevention, and treatment of diseases such as cancer, AMD, diabetic retinopathy, and other diseases derived from pathological angiogenesis.

WO 2005/007198 describes methods for making and screening antibodies specific for diagnosis and treatment of diseases that are associated with isoforms of a protein. This disclosure teaches making and screening antibodies that will recognize the amino acids of the splice junction of those exons that are specific to an isoform of various polypeptides associated with a disease state, inter alia VEGF isoforms. Proposed anti VEGF antibodies that would recognize either VEGF$_{121}$ or VEGF$_{165}$ isoforms are disclosed wherein the anti VEGF$_{121}$ specific antibodies would be raised against a peptide sequence of the junction between exons 5 and 8 (SEQ ID NO:6) and anti VEGF$_{165}$ specific antibodies would be raised against a peptide domain of the junction between exons 5 and 7.

None of the known antibodies that recognize an amino acid sequence shared by pro-angiogenic forms of VEGF, would discriminate between pro-angiogenic and anti-angiogenic forms of this growth factor. Thus, there is an unmet need to provide antibodies against VEGF which can be used diagnostically for discrimination between pro and anti-angiogenic isoforms and therapeutically for inhibiting only pro-angiogenic VEGF isoforms.

SUMMARY OF THE INVENTION

The present invention is based on the concept that currently available antibodies against VEGF not only neutralize the agonistic forms of VEGF but also neutralize the antagonist (anti-angiogenic) forms of VEGF and therefore act as mixed antagonists-agonists with the clinical response depending on the balance of VEGF isoforms present in the tissue. The present invention thus provides for the first time antibodies specific to pro angiogenic VEGF which can discriminate between the pro- and anti-angiogenic variants and neutralize only the former isoforms. The present invention also provides methods for obtaining such antibodies, methods for their production, and therapeutic and diagnostic uses thereof.

Specific peptidic sequences of VEGF, for example sequences encoded by exon 8a including the sequence CDKPRR (SEQ ID NO:1), are present in most pro-angiogenic VEGF variants but are absent in the VEGF antagonist variants which contain the sequence SLTRKD (SEQ ID NO:2) encoded by exon 8b. According to the present invention antibodies directed against antigenic determinants comprising sequences encoded by exon 8a, capable of discriminating between pro- and anti-angiogenic forms of VEGF are provided.

According to one aspect, the present invention provides antibodies against agonist isoforms of VEGF (also designated herein anti-VEGFxxx antibodies), capable of binding pro-angiogenic VEGF isoforms and not capable of binding anti-angiogenic VEGF forms.

According to one embodiment the antibody is an antibody specific to VEGF or an antibody fragment thereof comprising at least an antigen-binding portion, wherein said antibody recognizes an antigenic determinant comprising the epitope CDKPRR (SEQ ID NO:1).

According to specific embodiments the antibody recognizes an antigenic determinant selected from the group consisting of: CDKPRR (SEQ ID NO:1), RCDKPRR (SEQ ID NO:3), CRCDKPRR (SEQ ID NO:4), and TCRCDKPRR (SEQ ID NO:5).

According to yet another embodiment the antibodies do not bind VEGF isoforms comprising the sequence SLTRKD (SEQ ID NO:2). According to specific embodiments, the VEGF isoforms comprising the sequence SLTRKD are $VEGF_{165}b$ and $VEGF_{121}b$. $VEGF_{145}b$, $VEGF_{189}b$ $VEGF_{206}b$.

According to another embodiment, the antibodies are capable of binding a VEGF isoform comprising the sequence CDKPRR (SEQ ID NO:1) wherein the antigenic determinant of said antibodies does not include DRARQEK (SEQ ID NO:7).

According to one embodiment of the present invention, the antibody is a monoclonal antibody. According to a specific embodiment the monoclonal antibody is selected from the group consisting of: humanized antibody, human antibody, chimeric antibody and an antibody fragment comprising at least the antigen-binding portion of an antibody. According to a specific embodiment the antibody fragment is selected from the group consisting of: Fab, Fab', F(ab')$_2$, Fd, Fd', Fv, dAb, isolated CDR region, single chain antibody, "diabodies", and "linear antibodies".

According to a specific embodiment the monoclonal antibody is produced by a hybridoma cell line selected from the group consisting of: MR93 A26 clone 13-8-8 Deposit Number 08101401; MR93 A26 clone 13-8-10 Deposit Number 08101402; MR93 A26 clone 13-8-3 Deposit Number 08101403; deposited with the European Collection of Cell Cultures (ECACC). The deposits were made on Oct. 14, 2008 with the ECACC, Health Protection Agency, Center for Emergency Preparedness and Response, Porton Down, Salisbury SP4 0JG.

According to another embodiment the antibodies are polyclonal antibodies.

Within the scope of the present invention are also nucleic acid molecules encoding an antibody according to the invention, having affinity and specificity for agonistic VEGF isoforms.

According to this aspect, an isolated polynucleotide encoding an antibody specific to agonist isoforms of VEGF or an antibody fragment thereof is disclosed. According to a specific embodiment the antibody specific to agonist isoforms of VEGF or the antibody fragment thereof comprising at least an antigen-binding portion, recognizes an antigenic determinant comprising the epitope CDKPRR (SEQ ID NO:1).

In another aspect the present invention is related to a pharmaceutical composition useful for preventing, attenuating or treating a disease or disorder associated with VEGF. A pharmaceutical composition according to the invention comprises a therapeutically effective amount of an antibody capable of binding a pro-angiogenic VEGF form and unable to bind an anti-angiogenic VEGF form; and a pharmaceutically acceptable carrier.

According to one embodiment the pharmaceutical composition comprises a therapeutically effective amount of an antibody specific to agonist VEGF or an antibody fragment thereof comprising at least an antigen-binding portion. According to a specific embodiment the antibody specific to agonist VEGF or the antibody fragment thereof comprising at least an antigen-binding portion, recognizes an antigenic determinant comprising the epitope CDKPRR (SEQ ID NO:1).

According to specific embodiments the pharmaceutical composition comprises a therapeutically effective amount of an antibody specific to agonist VEGF or an antibody fragment thereof which recognize an antigenic determinant selected from the group consisting of CDKPRR (SEQ ID NO:1), RCDKPRR (SEQ ID NO:3), CRCDKPRR (SEQ ID NO:4), and TCRCDKPRR (SEQ ID NO:5).

According to certain embodiments the disease or disorder associated with agonist VEGF is a cell proliferative, a hyperpermeability or an angiogenesis-related disease or disorder (including but not limited to nephrotic syndrome and acute respiratory distressed syndrome, ARDS). According to other embodiments the cell proliferative disease or disorder is selected from the group including but not limited to: cancer, cell proliferative diseases of the eye (ocular diseases), retinal disorders, rheumatoid arthritis, and psoriasis.

Retinal disorders include for example, Choroidal Neovascular Membrane (CNVM), diabetic retinopathy, macular oedema, vascular occlusion, age-related macular degeneration (AMD), and retinopathy of prematurity (ROP).

In yet another aspect the present invention is related to a method of preventing, attenuating or treating a disease or disorder associated with angiogenesis or vascular endothelial cell proliferation, comprising administering to a subject in need thereof a pharmaceutical composition comprising a therapeutically effective amount of an antibody specific to agonistic isoforms of VEGF; and a pharmaceutically acceptable carrier.

According to some embodiments the disease or disorder associated with over expression of agonistic VEGF is an angiogenesis or a cell proliferative disease or disorder.

The pharmaceutical composition according to the present invention may be administered as a stand alone treatment or in addition to a treatment with any VEGF antagonist, including but not limited to an anti-angiogenic VEGF isoform. According to a specific embodiment, antibodies according to the present invention are administered to a subject in need thereof as part of a treatment regimen in conjunction with at least one anti-angiogenic isoform. According to specific embodiments the VEGF antagonist isoform is selected from the group consisting of: $VEGF_{165}b$, $VEGF_{121}b$, $VEGF_{145}b$ $VEGF_{189}b$ or $VEGF_{206}b$, and any combinations of these. The pharmaceutical composition according to the present invention may be administered together with the VEGF antagonist or separately.

The pharmaceutical composition according to the present invention may be administered together with an anti-neoplastic composition. According to a specific embodiment the anti-neoplastic composition comprises at least one chemotherapeutic agent. The chemotherapy agent, which could be administered together with the antibody according to the present invention, or separately, may comprise any such agent known in the art exhibiting anticancer activity, including but not limited to: mitoxantrone, topoisomerase inhibitors, spindle poison vincas: vinblastine, vincristine, vinorelbine (taxol), paclitaxel, docetaxel; alkylating agents: mechlorethamine, chlorambucil, cyclophosphamide, melphalan, ifosfamide; methotrexate; 6-mercaptopurine; 5-fluorouracil, cytarabine, gemcitabin; podophyllotoxins: etoposide, irinotecan, topotecan, dacarbazin; antibiotics: doxorubicin (adriamycin), bleomycin, mitomycin; nitrosoureas: carmustine (BCNU), lomustine, epirubicin, idarubicin, daunorubicin; inorganic ions: cisplatin, carboplatin; interferon, asparaginase; hormones: tamoxifen, leuprolide, flutamide, and megestrol acetate.

According to a specific embodiment, the chemotherapeutic agent is selected from the group consisting of alkylating agents, antimetabolites, folic acid analogs, pyrimidine analogs, purine analogs and related inhibitors, vinca alkaloids, epipodopyllotoxins, antibiotics, L-asparaginase, topoisomerase inhibitor, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. According to another embodiment, the chemotherapeutic agent is selected from the group consisting of 5-fluorouracil (5-FU), leucovorin (LV), irenotecan, oxaliplatin, capecitabine, paclitaxel and doxetaxel. Two or more chemotherapeutic agents can be used in a cocktail to be administered in combination with administration of the anti-VEGF antibody. One preferred combination chemotherapy is fluorouracil-based, comprising 5-FU and one or more other chemotherapeutic agent(s).

According to a specific embodiment, the invention provides a method of treating cancer in a subject, comprising administering to the subject effective amounts of an anti agonist VEGF antibody together with an anti-neoplastic composition.

The cancer amendable for treatment by the present invention include, but not limited to, carcinoma, lymphoma, blastoma, sarcoma, and leukemia or lymphoid malignancies. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. More preferably, the cancer is colorectal cancer. The cancerous conditions amendable for treatment of the invention include metastatic cancers. The method of the present invention is particularly suitable for the treatment of vascularized tumors.

In another aspect, the present invention provides a method for increasing the duration of survival of a subject having cancer, comprising administering to the subject effective amounts of a composition comprising an antibody specific to agonist isoforms of VEGF and an anti-neoplastic composition, wherein said anti-neoplastic composition comprises at least one chemotherapeutic agent, whereby the co-administration of the anti-VEGF antibody and the anti-neoplastic composition effectively increases the duration of survival.

In yet another aspect, the present invention provides a method for increasing the progression free survival of a subject having cancer, comprising administering to the subject effective amounts of a composition comprising an antibody specific to agonist isoforms of VEGF and an anti-neoplastic composition, wherein said anti-neoplastic composition comprises at least one chemotherapeutic agent, whereby co-administration of the antibody specific to agonist isoforms of VEGF and the anti-neoplastic composition effectively increases the duration of progression free survival.

Furthermore, the present invention provides a method for treating a subject having cancer, comprising administering to the subject effective amounts of a composition comprising an antibody specific to agonist isoforms of VEGF and an anti-neoplastic composition whereby co-administration of the antibody specific to agonist isoforms of VEGF and the anti-neoplastic composition effectively increases the response incidence in the group of subjects.

In yet another aspect, the present invention provides a method for increasing the duration of response of a subject having cancer, comprising administering to the subject effective amounts of a composition comprising an antibody against agonist isoforms of VEGF and an anti-neoplastic composition, wherein said anti-neoplastic composition comprises at least one chemotherapeutic agent, whereby co-administration of the antibody against agonist isoforms of VEGF and the anti-neoplastic composition effectively increases the duration of response.

Another aspect of the present invention relates to the use of an antibody specific to agonist isoforms of VEGF or an antibody fragment thereof, for the manufacture of a therapeutic composition for the treatment of a cell proliferative or angiogenesis-related disease or disorder.

According to one embodiment, the present invention provides use of an antibody specific to VEGF or an antibody fragment thereof comprising at least an antigen-binding portion, wherein said antibody recognizes an antigenic determinant comprising the epitope CDKPRR (SEQ ID NO:1), for preparation of a medicament for treatment of a disorder or disease associated with over-expression of angiogenic forms of VEGF, including but not limited to angiogenesis-related disease or disorder.

According to another aspect the present invention provides use of an antibody specific to VEGF or an antibody fragment thereof comprising at least an antigen-binding portion, wherein said antibody recognizes an antigenic determinant comprising the epitope CDKPRR (SEQ ID NO:1) for treatment of a disorder or disease associated with angiogenic forms of VEGF. According to one embodiment, the disease or disorder is angiogenesis or a cell proliferative disease or disorder.

Pro angiogenic VEGFs, denoted herein as VEGFxxx, are podocytes survival factors, pro-angiogenic and increase the permeability of glomeruli in the kidney, creating leaky glomeruli.

Anti angiogenic forms of VEGF denoted herein as VEGFxxxb, and exemplified by VEGF165b are podocyte survival factors, anti-angiogenic and decrease the permeability of human glomeruli.

VEGF scavengers such as AVASTIN®, and VEGR blockers (tyrosine kinase inhibitors, TKIs) such as SUTENT®, induce proteinuria and kidney impairment.

It is envisaged according to the principles of the present invention that nephritic damage and/or glomerular injury induced by TKIs such as SUTENT® or antibodies such as AVASTIN® may be avoided or ameliorated by treatment with antibodies specific only to the proangiogenic VEGFxxx.

It is envisaged according to the principles of the present invention that nephritic damage and/or glomerular injury induced by TKIs such as SUTENT® or antibodies such as AVASTIN® may be attenuated by treatment with VEGF165b. Thus, according to another aspect of the present invention VEGF 165b can attenuate the damage induced by the known VEGF scavengers and VEGFR blockers.

According to another aspect, the present invention provides a method of treating a subject in need thereof, comprising administering an antibody specific to pro-angiogenic VEGF forms according to the present invention, in conjunction with an anti angiogenic isoforms of VEGF.

According to a specific embodiment the anti angiogenic isoform of VEGF is $VEGF_{165}b$. According to other embodiments the anti angiogenic isoform of VEGF is selected from the group consisting of $VEGF_{121}b$. $VEGF_{145}b$, $VEGF_{189}b$, and $VEGF_{206}b$.

According to yet another aspect, the present invention provides a method of treating a renal disorder, comprising administering to a subject in need thereof an anti angiogenic isoforms of VEGF.

According to a specific embodiment the anti angiogenic isoform of VEGF is $VEGF_{165}b$. According to other embodiments the anti angiogenic isoform of VEGF is selected from the group consisting of $VEGF_{121}b$. $VEGF_{145}b$, $VEGF_{189}b$, and $VEGF_{206}b$.

According to another aspect of present invention a method for detecting or quantifying the presence of pro-angiogenic VEGF forms in is provided. Thus, the present invention also provides methods for diagnosing conditions associated with elevated levels of agonist VEGF isoforms using antibodies against agonist isoforms of VEGF. Diagnostic methods according to the invention may be performed according to specific embodiments in-vitro or ex-vivo. The antibodies according to the present invention may be also used to configure screening methods. For example, an ELISA assay can be constructed for measuring secreted or cell associated levels of polypeptide using monoclonal and polyclonal antibodies by standard methods known in the art.

According to one embodiment a method is provides for detecting or quantifying the presence of pro-angiogenic VEGF forms, comprising the steps of:
 i. incubating a sample with an antibody specific to agonist isoforms of VEGF or an antibody fragment thereof comprising at least an antigen-binding portion;
 ii. detecting the bound agonist VEGF using a detectable probe;
 iii. comparing the amount of (ii) to a standard curve obtained from reference samples containing known amounts of pro-angiogenic VEGF; and
 iv. calculating the amount of the pro-angiogenic antibody in the body fluid sample from the standard curve.

According to another embodiment a method for diagnosing a disease or disorder associated with pro-angiogenic VEGF forms is provided comprising the steps of
 i. incubating a biological sample with an antibody specific to agonist isoforms of VEGF or an antibody fragment thereof comprising at least an antigen-binding portion;
 ii. detecting the bound agonist VEGF using a detectable probe;
 iii. comparing the amount of (ii) to a standard curve obtained from reference samples containing known amounts of pro-angiogenic VEGF;
 iv. calculating the amount of the pro-angiogenic antibody in the body fluid sample from the standard curve; and
 v. comparing the amount of (iv) to a normal amount pro-angiogenic VEGF amount.

The antibodies of the present invention may be also used in screening assays for assessing the pro-angiogenic/anti-angiogenic ratio in patients and for prediction of the effectiveness of treatment with anti-VEGF therapies, such as known anti VEGF antibodies (for example treatment with AVASTIN®). The screening assays with the antibodies of the present invention may allow determination of the ratio between the pro and anti angiogenic forms of VEGF and therefore prediction of treatment outcome and planning of an appropriate treatment regimen. The ratio between the pro- and anti angiogenic forms of VEGF as measured by specific antibodies could be used as a predictive tool to estimate which patients might benefit from AVASTIN® or other anti-pan VEGF treatment such as VEGF-trap.

Essentially all of the uses known or envisioned in the prior art for VEGF anti-angiogenic/antagonist can be accomplished with the antibodies of the present invention. These uses include diagnostic, prophylactic and therapeutic techniques.

Further embodiments and the full scope of applicability of the present invention will become apparent from the detailed description given hereinafter.

BRIEF DESCRIPTION OF THE FIGURES

FIG. 3 describes inhibition of $VEGF_{165}$ mediated HUVEC migration by increasing concentrations of the monospecific polyclonal antibodies against Exon8a.

Human conditionally immortalized glomerular endothelial cells were serum starved for 2 hours then glomerular trans-endothelial electrical resistance in cultured monolayers was measured in response to either nothing (control), 1 nM VEGF165, 1 nM VEGF165b or a combination of 1 nM VEGF165 & 1 nM VEGF165b. Results are mean fold increase relative to the control (I.e. time point 0 min, SEM). n=5, Data analysis with prism: p±<0.0001, one way ANOVA, repeat measures, with Bonferroni post test. Control vs VEGF165 p<0.001, Control vs VEGF165b p, 0.01, control vs both p>0.05, VEGF165 vs VEGF165b and both p<0.001, VEGF165b vs both p<0.01. Data analysis using SSPS, overall p value >0.0005 one way ANOVA, repeat measures, Post hoc Bonferroni Control vs VEGF 0.001, vs others NSVEGF vs other three groups all significant 165 vs both 0.037

Figure 11:
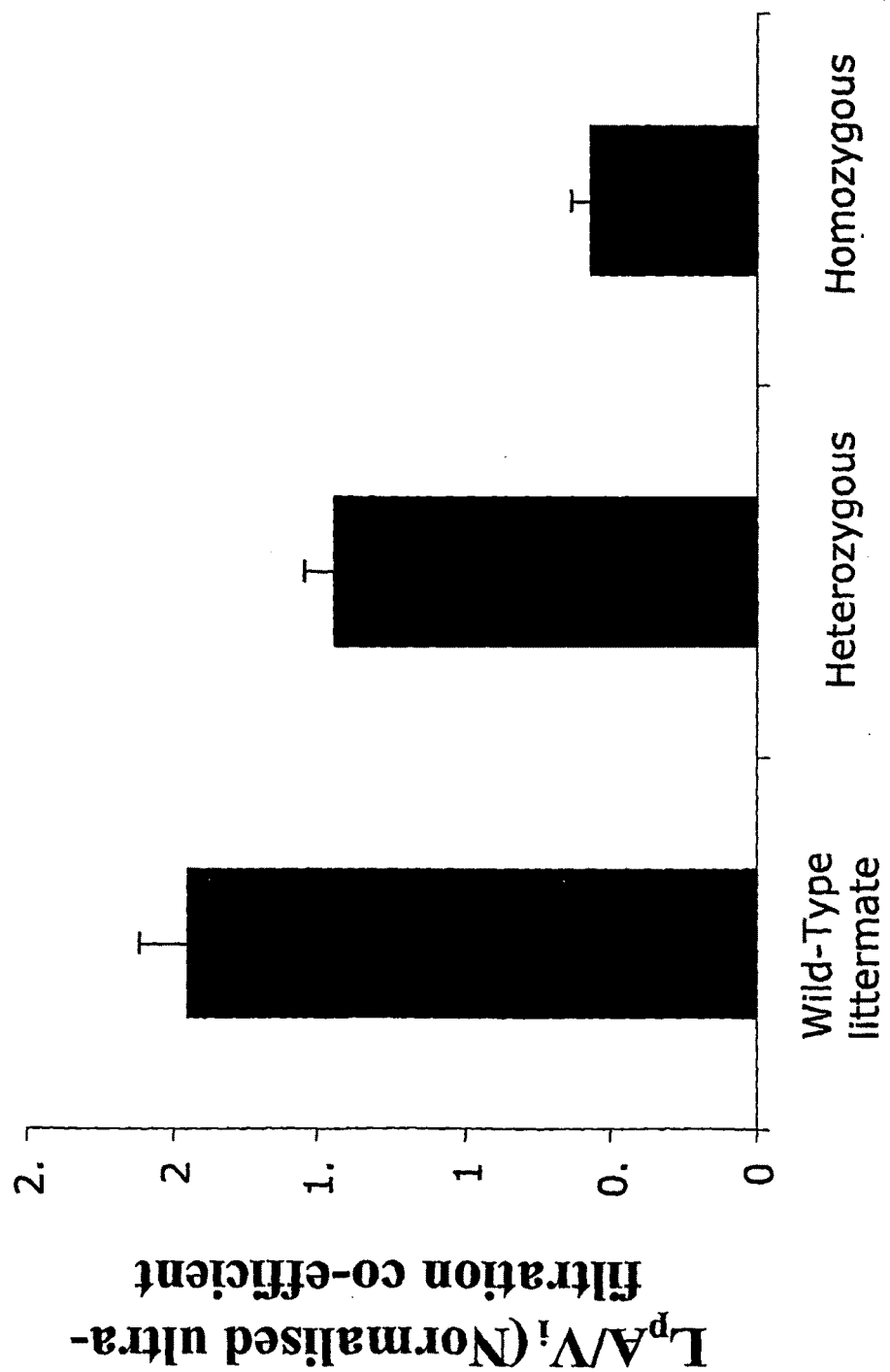

FIG. 11 describes LpA/Vi of intact ex vivo glomeruli in nephrin VEGF165b over-expressing transgenic mice.

DETAILED DESCRIPTION OF THE INVENTION

The present invention provides for the first time antibodies which are specific to the deleterious forms of VEGF but which can not neutralize the valuable antagonist forms of the protein. This was possible due to the structural differences between the anti-angiogenic/antagonist and pro-angiogenic/agonist forms of VEGF. For example, the natural VEGF anti-angiogenic/antagonist $VEGF_{165}b$ lacks the sequence encoded by exon 8a which is present in most pro-angiogenic forms of VEGF.

The antibodies produced against exon 8a were shown to bind and inhibit the pro-angiogenic isoform $VEGF_{165}$ but not the anti-angiogenic form $VEGF_{165}b$. These antibodies also inhibit $VEGF_{165}$ mediated HUVEC migration in a dose dependent manner.

VEGF is known to act as a pleiotropic factor. It not only regulates angiogenesis but also serves as a survival factor for many cells and tissue in the body such as neurons, retinal pigmented cells, podocytes in the kidney and normal and mature blood vessels. A completed depletion of VEGF such as the one that is achieved by antibodies that do not distinguish between the pro and anti angiogenic forms of VEGF and VEGFR blockers might expose patients to retinal damage, bleeding and proteinuria and kidney impairment and additional serious adverse events.

Antibodies targeted against the pro-angiogenic form of VEGF are expected to be safer and more efficacious since they scavenge the proangiogenic form of VEGF allowing the anti-angiogenic form of VEGF to bind the VEGFR1 and VEGFR2 and exert anti-angiogenesis and cells protection.

AVASTIN®, the anti VEGF antibody currently used in therapy, binds indiscriminately both forms of VEGF (pro and anti angiogenic) with the same affinity. This could explain its marginal efficacy and low safety profile. Treatment of patients with tumors expressing significant levels of $VEGF_{165}b$ with AVASTIN® may not be effective since $VEGF_{165}b$ will inhibit the effect of this anti VEGF antibody. The ratio between the pro- and anti angiogenic forms of VEGF as measured by specific antibodies according to the present invention, could be used as a predictive tool to forecast which patients might benefit from AVASTIN® or other anti-pan VEGF treatment such as VEGF-trap.

DEFINITIONS

The term "VEGF" is used to refer to (but not only) the 121-, 145-, 165-, 189-, and 206-amino acid vascular endothelial cell growth factors, as described by Leung et al. Science, 1989, 246, 1306, and Houck et al. Mol. Endocrin., 1991, 5, 1806, together with the naturally occurring allelic and processed forms thereof. The term "VEGF" is used to refer to all forms of VEGF-A e.g. truncated forms of the polypeptide comprising amino acids 8 to 109 or 1 to 109 of the 165-amino acid human vascular endothelial cell growth factor, the VEGF family and to the anti-angiogenic forms $VEGF_{165}b$, $VEGF_{121}b$ and the whole $VEGF_{xxx}b$ series.

The term "VEGF agonist", "agonistic VEGF" or "agonist of VEGF" refer to the pro-angiogenic activity of VEGF namely to VEGF forms which can promote or accelerate angiogenesis and/or permeability. Exemplary agonistic VEGF forms are those containing the sequence CDKPRR (SED ID NO:1) encoded by exon 8a.

The term "VEGF antagonistic" or "antagonist of VEGF" refer to VEGF forms which act as anti-angiogenic molecules and which are not capable of promoting angiogenesis. Exemplary agonistic VEGF forms are those containing the sequence SLTRKD (SEQ ID NO:2) encoded by exon 8b instead of the sequence CDKPRR (SEQ ID NO: 1) encoded by exon 8a.

Agonistic and antagonistic forms of VEGF are typically distinguished by having sequences expressed by Exon 8a (agonist VEGF form) or lacking Exon 8a and having Exon 8b expressed sequences, nevertheless, other forms of agonistic and antagonistic VEGF may exist and antibodies which distinguish between these agonistic and antagonistic forms are also included in the scope of the present invention. An "anti-VEGF antibody" is an antibody that binds to VEGF with sufficient affinity and specificity. Preferably, the anti-VEGF antibody of the invention can be used as a therapeutic agent in targeting and interfering with diseases or conditions wherein the VEGF activity is involved. An anti-VEGF antibody will usually not bind to other VEGF homologues such as VEGF-B, VEGF-C, VEGF-D or VEGF-E or other growth factors such as P1GF, PDGF or bFGF. The anti-VEGF antibody may be a recombinant humanized anti-VEGF monoclonal antibody.

An "antigen" is a molecule or a portion of a molecule capable of eliciting antibody formation and being bound by an antibody. An antigen may have one or more than one epitope. The specific reaction referred to above is meant to indicate that the antigen will react, in a highly selective manner, with its corresponding antibody and not with the multitude of other antibodies which may be evoked by other antigens. An antigen according to the present invention is an agonistic form of VEGF or a fragment thereof.

The term "antigenic determinant" or "epitope" according to the invention refers to the region of an antigen molecule that specifically reacts with particular antibody.

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (Fragment variable) and Fc (fragment crystalline) domains. The antigen binding domains, Fab, include regions where the polypeptide sequence varies. The term $F(ab')_2$ represents two Fab' arms linked together by disulfide bonds. The central axis of the antibody is termed the Fc fragment. Each heavy chain has at one end a variable domain ($V_H$) followed by a number of constant domains ($C_H$). Each light chain has a variable domain ($V_L$) at one end and a constant domain ($C_L$) at its other end, the light chain variable domain being aligned with the variable domain of the heavy chain and the light chain constant domain being aligned with the first constant domain of the heavy chain (CH1). The variable domains of each pair of light and heavy chains form the antigen-binding site. The domains on the light and heavy chains have the same general structure and each domain comprises four framework regions, whose sequences are relatively conserved, joined by three hypervariable domains known as complementarity determining regions (CDR1-3). These domains contribute specificity and affinity of the antigen-binding site. The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ) found in all antibody classes.

The term "antibody" is used in the broadest sense and includes monoclonal antibodies (including full length or intact monoclonal antibodies), polyclonal antibodies, multivalent antibodies, multispecific antibodies (e.g., bispecific antibodies), and antibody fragments so long as they exhibit the desired biological activity.

The antibody according to the present invention is a molecule comprising at least the antigen-binding portion of an antibody. Antibody or antibodies according to the invention include intact antibodies, such as polyclonal antibodies or monoclonal antibodies (mAbs), as well as proteolytic fragments thereof such as the Fab or F(ab')$_2$ fragments. Further included within the scope of the invention are chimeric antibodies; human and humanized antibodies; recombinant and engineered antibodies, and fragments thereof. Furthermore, the DNA encoding the variable region of the antibody can be inserted into the DNA encoding other antibodies to produce chimeric antibodies. Single chain antibodies also fall within the scope of the present invention.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 1989, 341, 544-546) which consists of a VH domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., Science 1988, 242, 423-426; and Huston et al., PNAS (USA) 1988, 85, 5879-5883); (x) "diabodies" with two antigen binding sites, comprising a heavy chain variable domain (VII) connected to a light chain variable domain (VL) in the same polypeptide chain (see, e.g., EP 404,097; WO 93/11161; and Hollinger et al., Proc. Natl. Acad. Sci. USA, 1993, 90, 6444-6448); (xi) "linear antibodies" comprising a pair of tandem Fd segments (VH-CH1-VH-CH1) which, together with complementary light chain polypeptides, form a pair of antigen binding regions (Zapata et al. Protein Eng., 1995, 8, 1057-1062; and U.S. Pat. No. 5,641,870).

Single chain antibodies can be single chain composite polypeptides having antigen binding capabilities and comprising amino acid sequences homologous or analogous to the variable regions of an immunoglobulin light and heavy chain i.e. linked $V_H$-$V_L$ or single chain Fv (scFv).

A "neutralizing antibody" as used herein refers to a molecule having an antigen-binding site to a specific receptor or ligand target capable of reducing or inhibiting (blocking) activity or signaling through a receptor, as determined by in vivo or in vitro assays, as per the specification.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. mAbs may be obtained by methods known to those skilled in the art. For example, the monoclonal antibodies to be used in accordance with the present invention may be made by the hybridoma method first described by Kohler et al., Nature 1975, 256, 495, or may be made by recombinant DNA methods (see, e.g., U.S. Pat. No. 4,816,567). The "monoclonal antibodies" may also be isolated from phage antibody libraries using the techniques described in Clackson et al., Nature 1991, 352, 624-628 or Marks et al., J. Mol. Biol., 1991, 222:581-597, for example.

The mAbs of the present invention may be of any immunoglobulin class including IgG, IgM, IgE, IgA, and any subclass thereof. A hybridoma producing a mAb may be cultivated in vitro or in vivo. High titers of mAbs can be obtained in vivo production where cells from the individual hybridomas are injected intraperitoneally into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). In addition, complementarity determining region (CDR) grafting may be performed to alter certain properties of the antibody molecule including affinity or specificity. A non-limiting example of CDR grafting is disclosed in U.S. Pat. No. 5,225,539.

Chimeric antibodies are molecules, the different portions of which are derived from different animal species, such as those having a variable region derived from a murine mAb and a human immunoglobulin constant region. Antibodies which have variable region framework residues substantially from human antibody (termed an acceptor antibody) and complementarity determining regions substantially from a mouse antibody (termed a donor antibody) are also referred to as humanized antibodies. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (for example PCT patent applications WO 86/01533, WO 97/02671, WO 90/07861, WO 92/22653 and U.S. Pat. Nos. 5,693,762, 5,693,761, 5,585,089, 5,530,101 and 5,225,539).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 1986, 321, 522-525; Riechmann et al., Nature 1988, 332, 323-329; and Presta, Curr. Op. Struct. Biol., 1992 2, 593-596.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. Nature Biotechnology 1996 14, 309-314; Sheets et al. PNAS (USA), 1998, 95, 6157-6162); Hoogenboom and Winter, J. Mol. Biol., 1991, 227, 381; Marks et al., J. Mol. Biol., 1991, 222, 581). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al, Bio/Technology 10: 779-783 (1992); Lonberg et al., Nature 368: 856-859 (1994); Morrison, Nature 368:812-13 (1994); Fishwild et al., Nature Biotechnology 14: 845-51 (1996); Neuberger, Nature Biotechnology 14: 826 (1996); Lonberg and Huszar, Intern. Rev. Immunol. 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., J. Immunol., 147 (1):86-95 (1991); and U.S. Pat. No. 5,750,373.

By the term "single chain variable fragment (scFv)" is meant a fusion of the variable regions of the heavy and light chains of immunoglobulin, linked together with a short (usually serine, glycine) linker. Single chain antibodies can be single chain composite polypeptides having antigen binding capabilities and comprising amino acid sequences homologous or analogous to the variable regions of an immunoglobulin light and heavy chain (linked $V_H$-$V_L$ or single chain Fv (scFv)). Both $V_H$ and $V_L$ may copy natural monoclonal antibody sequences or one or both of the chains may comprise a CDR-FR construct of the type described in U.S. Pat. No. 5,091,513, the entire contents of which are incorporated herein by reference. The separate polypeptides analogous to the variable regions of the light and heavy chains are held together by a polypeptide linker. Methods of production of such single chain antibodies, particularly where the DNA encoding the polypeptide structures of the $V_H$ and $V_L$ chains are known, may be accomplished in accordance with the methods described, for example, in U.S. Pat. Nos. 4,946,778, 5,091,513 and 5,096,815, the entire contents of each of which are incorporated herein by reference.

A "molecule having the antigen-binding portion of an antibody" as used herein is intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, Fab mini-antibodies (see WO 93/15210, U.S. patent application Ser. No. 08/256,790, WO 96/13583, U.S. patent application Ser. No. 08/817,788, WO 96/37621, U.S. patent application Ser. No. 08/999,554, the entire contents of which are incorporated herein by reference), dimeric bispecific mini-antibodies (see Muller et al., 1998) and chimeric or single-chain antibodies incorporating such reactive fraction, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

Antibodies according to the invention can be obtained by administering the agonistic VEGF, or epitope-bearing fragments, analogs, or cells expressing, to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., Nature 256: 495-497 (1975); Kozbor et al., Immunology Today 4: 72 (1983); Cole et al., pg. 77-96 in MONOCLONAL ANTIBODIES AND CANCER THERAPY, Alan R. Liss, Inc. (1985).

Besides the conventional method of raising antibodies in vivo, antibodies can be generated in vitro using phage display technology. Such a production of recombinant antibodies is much faster compared to conventional antibody production and they can be generated against an enormous number of antigens. Furthermore, when using the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast Finally, large numbers of different antibodies against a specific antigen can be generated in one selection procedure. To generate recombinant monoclonal antibodies one can use various methods all based on display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

Non-human antibodies may be humanized by any methods known in the art. In one method, the non-human complementarity determining regions (CDRs) are inserted into a human antibody or consensus antibody framework sequence. Further changes can then be introduced into the antibody framework to modulate affinity or immunogenicity.

For example, U.S. Pat. No. 5,585,089 of Queen et al. discloses a humanized immunoglobulin and methods of preparing same, wherein the humanized immunoglobulin comprises complementarity determining regions (CDRs) from a donor immunoglobulin and heavy and light chain variable region frameworks from human acceptor immunoglobulin heavy and light chains, wherein said humanized immunoglobulin comprises amino acids from the donor immunoglobulin framework outside the Kabat and Chothia CDRs, wherein the donor amino acids replace corresponding amino acids in the acceptor immunoglobulin heavy or light chain frameworks.

U.S. Pat. No. 5,225,539, of Winter, also discloses an altered antibody or antigen-binding fragment thereof and methods of preparing same, wherein a variable domain of the antibody or antigen-binding fragment has the framework regions of a first immunoglobulin heavy or light chain variable domain and the complementarity determining regions of a second immunoglobulin heavy or light chain variable domain, wherein said second immunoglobulin heavy or light chain variable domain is different from said first immunoglobulin heavy or light chain variable domain in antigen binding specificity, antigen binding affinity, species, class or subclass.

Anti-idiotype antibodies specifically immunoreactive with an antibody of the invention are also comprehended.

Techniques for the production of single chain antibodies (U.S. Pat. No. 4,946,778) can be adapted to produce single chain antibodies to polypeptides or polynucleotides of this invention. Also, transgenic mice, or other organisms such as other mammals, can be used to express humanized antibodies immunospecific to the polypeptides or polynucleotides of the invention.

Alternatively, phage display technology can be utilized to select antibody genes with binding activities towards a polypeptide of the invention either from repertoires of PCR amplified v-genes of lymphocytes from humans screened for possessing anti-VEGF or from libraries (McCafferty, et al., (1990), Nature 348, 552-554; Marks, et al., (1992) Biotechnology 10, 779-783). The affinity of these antibodies can also be improved by, for example, chain shuffling (Clackson et al., (1991) Nature 352:628).

The above-described antibodies can be employed to isolate or to identify clones expressing the polypeptides to purify the polypeptides by, for example, affinity chromatography.

The invention also provides conservative amino acid variants of the antibody molecules according to the invention. Variants according to the invention also may be made that conserve the overall molecular structure of the encoded proteins. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved.

A "disorder" is any condition that would benefit from treatment with the antibody. This includes chronic and acute disorders or diseases including those pathological conditions which predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal and blastocoelic disorders; and inflammatory, angiogenic, immunologic disorders or hyperpermeability states.

VEGF is known to promote vascular endothelial cell proliferation and angiogenesis which are important components of a variety of pathologies, therefore, the antibodies according to the present invention may be used against conditions including tumor growth and metastasis, rheumatoid arthritis, atherosclerosis and arteriosclerosis, neointimal hyperplasia, diabetic retinopathy and other complications of diabetes, trachoma, retrolental fibroplasia, neovascular glaucoma, age-related macular degeneration, trachoma haemangiomata, immune rejection of transplanted corneal tissue, corneal angiogenesis associated with ocular injury or infection, psoriasis, gingivitis and other conditions known to be associated with angiogenesis and/or chronic inflammation. The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

"Treatment" refers to both therapeutic treatment and prophylactic or preventative measures. Those in need of treatment include those already with the disorder as well as those in which the disorder is to be prevented.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

The term "anti-neoplastic composition" refers to a composition useful in treating cancer comprising at least one active therapeutic agent capable of inhibiting or preventing tumor growth or function, and/or causing destruction of tumor cells. Therapeutic agents suitable in an anti-neoplastic composition for treating cancer include, but not limited to, chemotherapeutic agents, radioactive isotopes, toxins, cytokines such as interferons, and antagonistic agents targeting cytokines, cytokine receptors or antigens associated with tumor cells. For example, therapeutic agents useful in the present invention can be antibodies such as anti-HER2 antibody and anti-CD20 antibody, or small molecule tyrosine kinase inhibitors such as VEGF receptor inhibitors and EGF receptor inhibitors. Preferably the therapeutic agent is a chemotherapeutic agent.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™ polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

Pharmacology

The present invention also contemplates pharmaceutical formulations for human medical use, which comprise as the active agent at least one antibody specific to agonist isoforms of VEGF, for the manufacture of a therapeutic composition for the treatment or prophylaxis of the conditions variously described herein.

In such pharmaceutical and medicament formulations, the active agent is preferably utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

Typically, the molecules of the present invention comprising the antigen binding portion of an antibody or comprising another polypeptide including a peptidomimetic will be suspended in a sterile saline solution for therapeutic uses. The pharmaceutical compositions may alternatively be formulated to control release of active ingredient (molecule comprising the antigen binding portion of an antibody) or to prolong its presence in a patient's system. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly(ethylene-co-vinyl acetate) and matrices of a polyanhydride copolymer of a stearic acid dimer and sebaric acid. The rate of release of the molecule according to the present invention, i.e., of an antibody or antibody fragment, from such a matrix depends upon the molecular weight of the molecule, the amount of the molecule within the matrix, and the size of dispersed particles.

The pharmaceutical composition of this invention may be administered by any suitable means, such as orally, topically, intranasally, subcutaneously, intramuscularly, intravenously, intra-arterially, intraarticulary, intralesionally or parenterally. Ordinarily, intravenous (i.v.), intraarticular, topical or parenteral administration will be preferred.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician. As used herein, a "therapeutically effective amount" refers to the amount of a molecule required to alleviate one or more symptoms associated with a disorder being treated over a period of time.

Although an appropriate dosage of a molecule of the invention varies depending on the administration route, type of molecule (polypeptide, polynucleotide, organic molecule etc.) age, body weight, sex, or conditions of the patient, and should be determined by the physician in the end, in the case of oral administration, the daily dosage can generally be between about 0.01 mg to about 500 mg, preferably about 0.01 mg to about 50 mg, more preferably about 0.1 mg to about 10 mg, per kg body weight. In the case of parenteral administration, the daily dosage can generally be between about 0.001 mg to about 100 mg, preferably about 0.001 mg to about 10 mg, more preferably about 0.01 mg to about 1 mg, per kg body weight. The daily dosage can be administered, for example in regimens typical of 1-4 individual administration daily. Other preferred methods of administration include intraarticular administration of about 0.01 mg to about 100 mg per kg body weight. Various considerations in arriving at an effective amount are described, e.g., in Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990.

Suitable dosing regimens of combination chemotherapies are known in the art and described in, for example, Saltz et al. Proc ASCO 1999, 18, 233a and Douillard et al., Lancet 2000, 355, 1041-7.

The molecules of the present invention as active ingredients are dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, pH buffering agents.

The following examples are intended to illustrate how to make and use the compounds and methods of this invention and are in no way to be construed as a limitation. Although the invention will now be described in conjunction with specific embodiments thereof, it is evident that many modifications and variations will be apparent to those skilled in the art. Accordingly, it is intended to embrace all such modifications and variations that fall within the spirit and broad scope of the appended claims.

EXAMPLES

Means for preparing and characterizing antibodies are well known in the art. A description follows as to exemplify techniques for the production of anti-VEGFxxx antibodies in accordance with the present invention. The VEGF antigen to be used for production of antibodies is any peptide sequences of VEGFxxx which is present in agonistic forms but absent in antagonistic forms of VEGF.

Example 1

Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Example 2

Production of Specific Polyclonal Antibodies Against $VEGF_{165}$

Polyclonal antibodies were designed to bind and inhibit the pro-angiogenic isoform VEGF165 but not the anti-angiogenic form $VEGF_{165}b$. The peptide RCDKPRR (SEQ ID NO:3), containing the seven C-terminal amino acid residues of $VEGF_{165}$ was coupled to KLH, through an amino hexanoic acid spacer, and used for immunizing rabbits. Sera containing polyclonal antibodies collected from the immunized rabbits.

Preparation of Peptide-KLH Conjugates for Immunization

Peptide thiol groups were checked before coupling, either to KLH or to resin, since peptide thiol groups have a tendency to get lost after synthesis.

1. A solution of 5 mM Ellman's reagent (dithio-bis-2-nitrobenzoic acid) in 0.1M NaPi pH 7.2 was prepared.
2. About 1 mg of peptide was weighted into a tared tube.
3. 0.5 ml reagent was added. The solution turned into bright yellow.
4. The mixture was diluted 1/50 in buffer. The absorption at 412 nm was read against reagent at the same concentration.
5. The apparent molecular weight of the peptide based on thiol groups, was calculated using a molar extinction coefficient of 14,000. The result was compared to the expected molecular weight of the peptide. The number should agree within a factor of three, with the apparent molecular weight usually higher. If the thiol concentration is anomalously low, i.e., the apparent molecular weight is very high, there may be something wrong with the peptide—anyway it probably will not couple well. The thiol groups should be then regenerated by reducing the peptide with excess DTT and running a P2 column.

Coupling of Peptide to KLH (for Two Rabbits, Five Injections Per Rabbit):

1. 100 mg of keyhole limpet hemocyanin (KLH) were dissolved in 2 ml water, sonicated and Vortexed and put on a rotator at 4° C. for about 4 hours.
2. The solution was dialyzed overnight against 2 liters of 0.1M NaPhoshate pH 7.8. This is to remove any contaminating thiols or amino compounds.
3. The solution was spined for 10 minutes at full speed in microfuge to remove aggregates.
4. The KLH solution was splited into two aliquots for —SH and —$NH_2$ coupling.
5. For —$NH_2$ coupling, 5 mg peptide were added to one aliquot, followed by glutaraldehyde addition to 0.1% final. The peptide was added as a solid or from a 100 mg/ml stock in DMSO. After adding the glut, the pH was checked with a pH paper, and adjusted to 7.8 using NaOH. The solution was incubated 8-12 hrs at 4° C., rotating gently.
6. A tiny pinch of NaBH4 was added to kill remaining glut (in a large tube since it tends to fizz up), and the solution was incubate 8-12 hrs at 4° C.
7. For the —SH coupling, the other aliquot of KLH was warmed to room temp. 1/9 the volume of Iodoacetic acid N-hydroxysuccinimide ester at 100 mg/ml in DMSO was added (the iodoacetamide reagent should be protected from light). The IAA-NHS ester could be also purchased from Sigma.
8. After 10 minutes at room temp the KLH start to get a little cloudy. It was loaded into a P-10 column equilibrated with 0.1M NaPhosphate pH 7.8 (the column is at least 10 times the volume of the sample). The KLH containing fractions were pooled by color (they were sort of greyish green). 5 mg of peptide was added, as in step 5 above. The solution was incubated at least 8 hrs at 4° C., rotating gently.
9. The coupled peptide from the two procedures was pooled, diluted to 5 ml with 0.15M NaCl and sonicated vigorously to break it up. The immunogen was split into 1 ml aliquots (each aliquot for immunization of two rabbits) and freeze.

Immunization was performed as following:

| Operation | Time |
| --- | --- |
| Pre-Immune Test bleed & immunization # 1 | 0 |
| immunization # 2 | 7 days |
| Test bleed # 1 | 14 days |
| immunization # 3 | 21 days |
| Test bleed # 2 | 28 days |
| immunization # 4 | 35 days |
| Test bleed # 3 | 42 days |
| immunization # 5 | 63 days |
| Harvest bleed | 70 days |

The pooled serum was affinity purified on a Peptide-KLH column which was prepared as following, to produce monospecific polyclonal antibody preparation:

Coupling of Peptide-KLH to NHS-Activated Resin

1. NHS-activated Sepharose® 4 Fast Flow is a pre-activated Agarose matrix. NHS (N-hydroxysuccinimide) coupling forms a chemically stable amide bond with ligands containing primary amino groups. NHS-activated Sepharose® 4 Fast Flow provides a spacer arm and is therefore particularly suitable for immobilizing small protein and peptide ligands. The high stability and a spacer arm combined with the high flow and stability characteristics of the resin make it attractive for pharmaceutical uses.
2. The coupled gel can is used to prepare affinity adsorbents which can isolate specific substances including KLH-coupled peptides antigens, achieving very high purity in a single step.
3. The coupling reaction is rapid and spontaneous NHS-activated Sepharose 4 Fast Flow is supplied as a suspension. Coupling a ligand to the activated matrix involves washing the gel followed by coupling.
4. The buffers used for the coupling are: Coupling buffer: 0.2M $NaHCO_3$, 0.5M NaCl, pH 8.3, Acidification solution: 1 mM HCl (kept cold), Blocking buffer: 0.5M Ethanolamine, 0.5M NaCl, pH 8.3, Wash buffer: 0.1M acetate, 0.5M NaCl, pH 4.0, Storage buffer: 20% ethanol/PBS, Equilibration buffer: PBS.

The affinity purified serum was finally ultrafiltrated using a Vivaspin instrument.

The specificity of the antibodies was determined by Western Blot analysis by incubation the antibody purified fraction with $VEGF_{165}$ and $VEGF_{165}b$.

Western Blot Protocol:

Blocking in 10% skim milk/PBS/0.05% tween over night;
Primary antibody—rabbit whole serum diluted 1:50 in 2.5% blocking solution for 2 hrs;
Second antibody—goat anti rabbit diluted 1:8000 in 2.5% blocking solution; and exposure to x-ray for 20 seconds.

Figure 1:
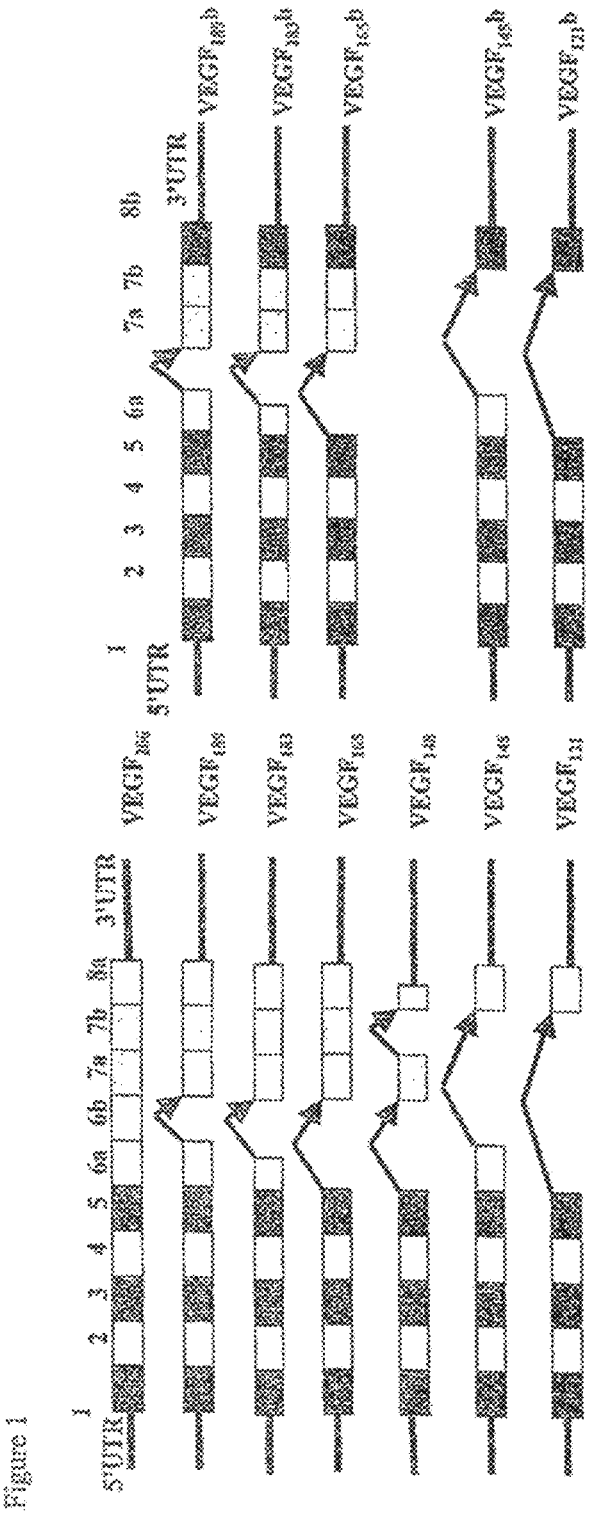
FIG. 1 is a schematic presentation of A) an exon map of the human VEGF gene, and B) the exon splicing patterns that lead to different VEGF isoforms.
Figure 2:
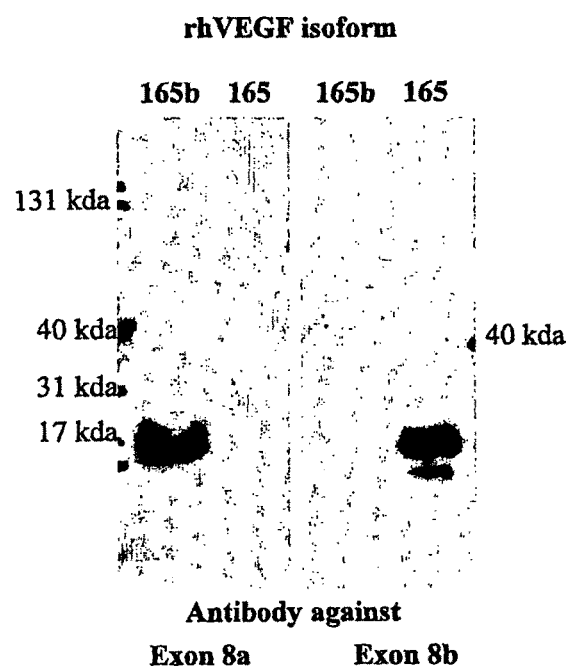
FIG. 2 represents a Western blot analysis of recombinant $VEGF_{165}$, and $VEGF_{165}b$ using affinity purified, monospecific polyclonal antibody to exon8a, or exon 8b.

As shown in FIG. 2 the affinity polyclonal antibody fraction (raised against the epitope of RCDKPRR (SEQ ID NO:3) of exon 8a) detects $VEGF_{165}$, but not $VEGF_{165}b$ (left panel), while antibody specific to $VEGF_{165}b$ (raised against the epitope SLTRKD (SEQ ID NO:2) of exon 8b) recognizes VEGF$_{165}$b but not VEGF$_{165}$ (right panel).

The purified antibodies are further assessed by:
ELISA (Perrin et al., diabetologia 2005, 48, 2422; Varey et al., British J. Cancer 2008, 1; Migration assay (as described in Bates et al., Cancer Research 2002, 62, 4123); Ocular angiogenesis (as described in Konopatskaya et al., Molecular Vision 2006, 26, 626); In vivo tumor studies as (as described in Rennel et al., Eur. J. Cancer 2008, 44, 1883); Immunohistochemistry (as described in Pritchard-Jones et al., Br. J. Cancer 2007, Br J Cancer, 97, 223.

Example 3

Polyclonal Antibodies Against VEGF$_{165}$ Inhibit Endothelial Cell Migration

Inhibition of migration was tested as described in Bates et al., Cancer Research 2002, 62, 4123-4131. The assays were performed in a modified 24-well Boyden chamber containing collagen-coated polycarbonate filter inserts (8 m pore; Millipore). The filters were placed in 24-well plates containing 0.5 ml/well of VEGF isoforms with or without 4-80 ng/ml purified antibody fraction. Human Umbilical Vein Endothelial Cells (HUVECs) were suspended in serum-free medium, and 25,000 cells were added to the upper chamber of each well. The plate was incubated for 6 h to allow migration, medium was removed, and both chambers were washed twice with PBS. 0.2 mg/ml thiazolyl blue (MTT) in medium was then added to both chambers and incubated for 3 h at 37° C. The medium was removed, and the chambers were washed twice with PBS. Non-migrated cell crystals in the upper chamber (stained blue) were removed with a cotton swab, which was placed in 1 ml of DMSO to dissolve the MTT product. Migratory cell crystals (on the underside of the insert) were also dissolved in MTT. The samples were left overnight to permit complete solution of the product. The absorbance of soluble MTT was determined at a wavelength of 570 nm using a spectrophotometer. The percentage migration was then calculated from the intensity of the lower well as a percentage of the total intensity of both wells.

Figure 3:
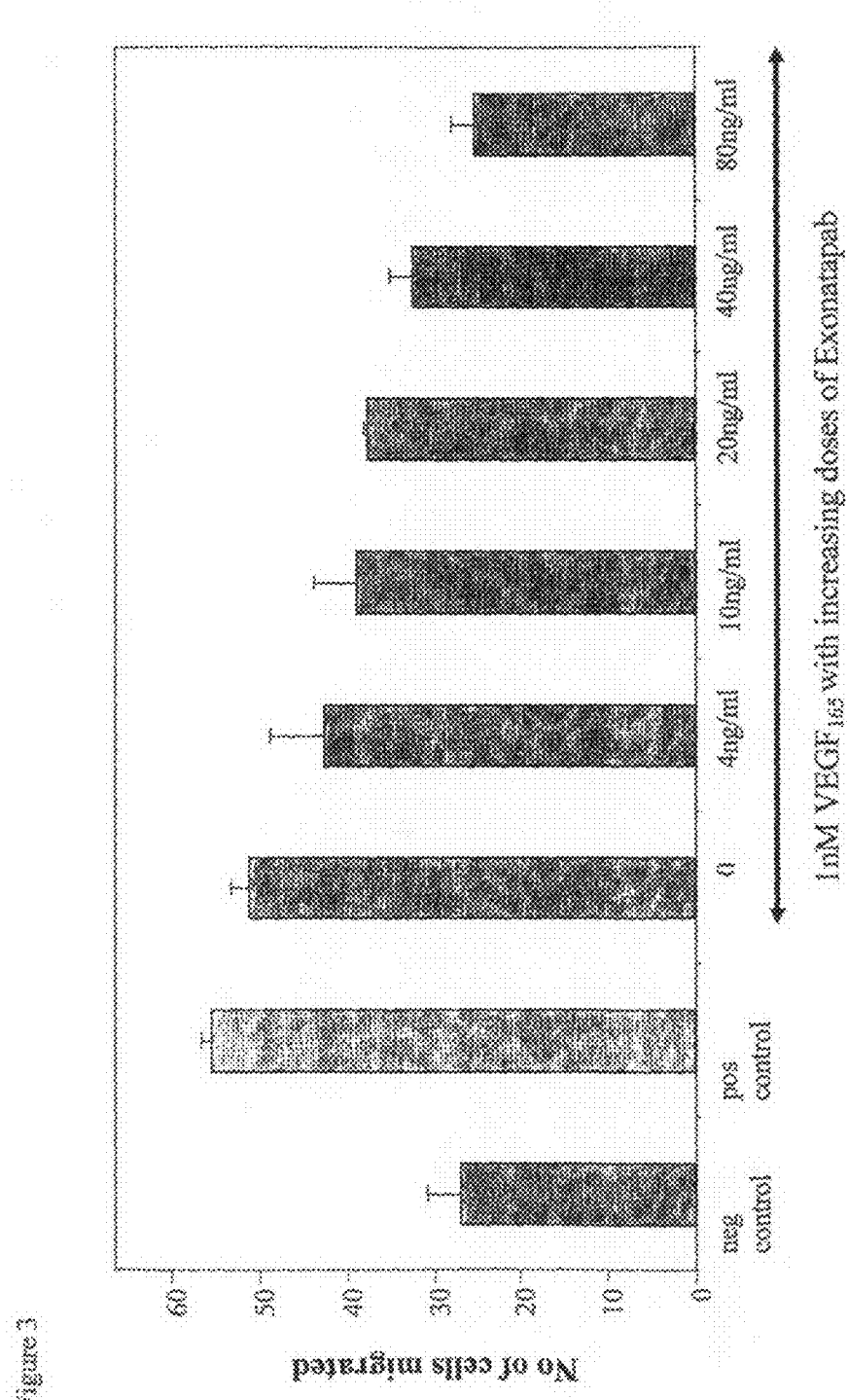

As shown in FIG. 3 increasing doses of the polyclonal antibody results in a dose dependent inhibition of VEGF$_{165}$ mediated HUVEC migration.

Figure 4A:
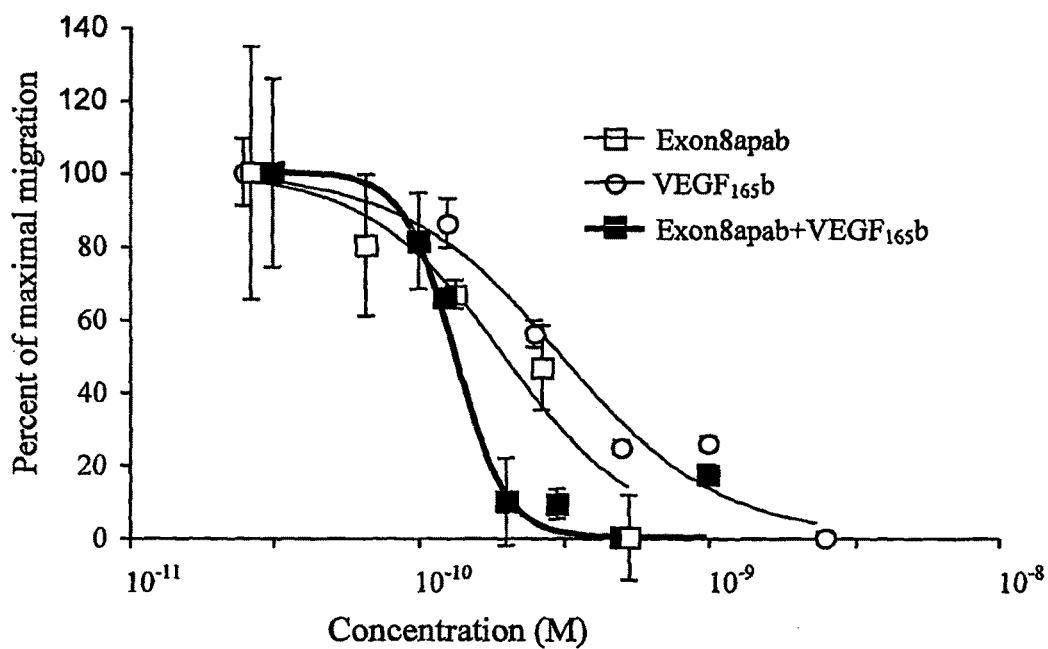
FIGS. 4A and 4B depict HUVEC migration measured in the presence of $VEGF_{165}b$, the monospecific polyclonal antibodies against Exon8a or the combination of both.
Figure 4B:
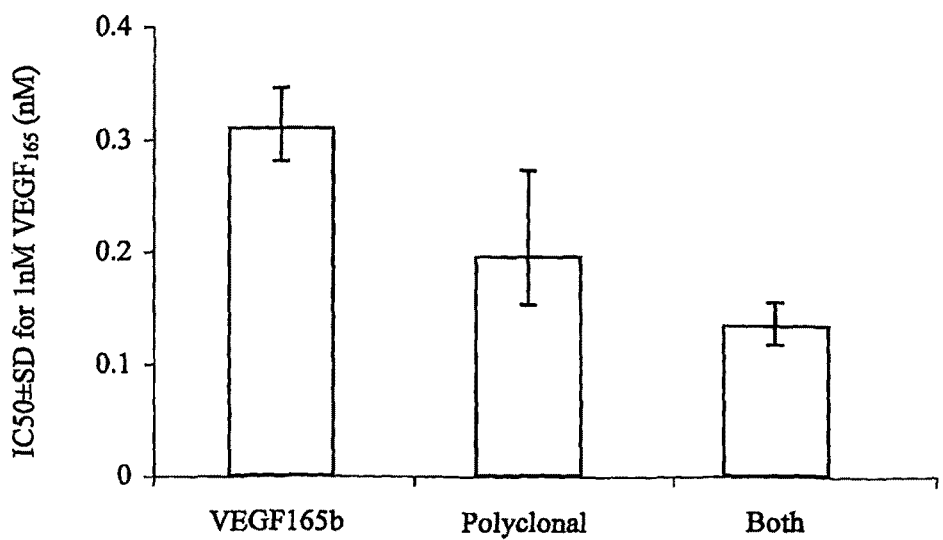
Figure 5:
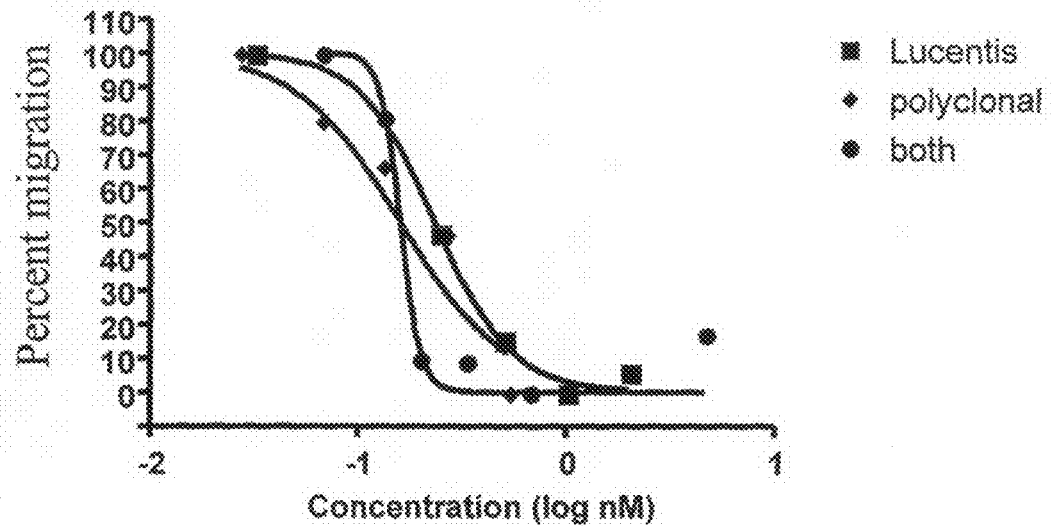
FIG. 5 describes HUVEC migration measured as above in the presence of $VEGF_{165}$, the monospecific polyclonal antibodies against Exon8a or Lucentis or the combination of polyclonal antibodies against Exon8a and $VEGF_{165}b$.

The effect of antibodies against Exon 8a on HUVEC migration was tested also in combination with VEGF$_{165}$b or Lucentis™ (an Fab antibody fragment of AVASTIN®). As shown in FIGS. 4A, 4B and 5 both VEGF$_{165}$b and Lucentis™ increase the inhibitory effect of polyclonal antibodies against Exon 8a. Furthermore, the inhibitory effect of polyclonal antibodies against Exon 8a in combination with VEGF$_{165}$b was greater than the inhibitory effect of AVASTIN®/lucentis in combination with VEGF$_{165}$b.

Example 4

Monoclonal Antibodies

Monoclonal antibodies may be made for example, using the hybridoma method first described by Kohler et al., Nature, 1975, 256:495, or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and WIC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty et al., Nature, 348: 552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783

(1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl. Acad. Sci. USA, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Example 5

Production of Specific Monoclonal Antibody to $VEGF_{xxx}$ Isoforms

Synthetic peptide fragments of the 6 and 9 amino acid C-terminal sequence of $VEGF_{165}$ (CDKPRR SEQ ID NO: 1, TCRCDKPRR SEQ ID NO:5) were coupled to keyhole limpet haemocyanin (KLH) (Department of Biochemistry, University of Bristol, UK) serving as carrier molecules and were then used to immunize 6-8 week old female Balb/c mice.

According to one protocol the animals were injected sub-cutaneously with 100 μg peptide-KLH conjugates in Freund's Complete Adjuvant (FCA) on days 1, 21 and 42 and boosted by i.p injection at 63, 64 and 65 days, separately. Mice were killed humanely the next day and spleens collected.

Additional immunization protocol was performed as following: 10 female Balb/C mice (6-8 weeks old) were ordered and have settled down in animal house for 1 week by the time of immunization. The above two VEGF 165 peptides (TCRCDKPRR SEQ ID NO:5) and CDKPRR SEQ ID NO:1) conjugated to KLH were used:
First Injection (time 0)—ten mice (five for each peptide) were injected sub-cutaneously with 100 μl (100 μg) peptide-KHL conjugate in Complete Freund's Adjuvant (CFA).
Second Injection (3 weeks later)—the mice were immunized inter-peritoneally (IP) with 100 μl (100 μg) peptide-KHL conjugate in Incomplete Freund'$_s$ Adjuvant (IFA).
Third Injection (3 weeks later)—the mice were immunized IP with 100 μl (100 μg) peptide-KHL conjugate in PBS.
Fourth Injection (1 day later)—the mice were immunized IP with 100 μl (100 μg) peptide-KHL conjugate in PBS.
Last Injection (1 day later)—the mice were immunized IP with 100 μl (100 μg) peptide-KHL conjugate in PBS.
Collection (1 day after last injection)—the immunized mice were scarified and transferred to Southmead Hospital, National Blood Service (NBS) for fusion.

Splenocytes were fused to the NS0 mouse myeloma cell line with polyethylene glycol. Fused cells were cultured in 96-well plates for 2 weeks. Cells from positive wells determined by ELISA screening were serially diluted in 96-well plates and cultured in 10% DMEM and hybridoma cloning enhancing factor. The same procedure was repeated until 100% positivity from each plate was achieved 3 consecutive times. Screening was done in Immulon II HB Flat well 96 well plates (Thermo Life Sciences Ld.), coated with goat anti-human VEGF antibody (0.8 μg/ml in PBS, R & D). After washing with PBS/T, 100 μl of 2 ng/ml $VEGF_{165}$ or recombinant $VEGF_{165}$b (R&D systems) was added to the wells and incubated for 15 min at 37° C. with shaking. After washing, 100 μl conditioned medium from hybridoma cells was added and incubated for 15 min at 37° C. with shaking. After washing, 100 μl of HRP-conjugated goat anti-mouse immunoglobulins (1:1000 in 1% BSA/PBS, DACO) were added and incubated for 15 min at 37° C. with shaking. After final washing, O-Phenylenediamine dihydrochloride, (OPD) substrate (Sigma Chemical Co., USA) was added and the absorbance at 492 nm was measured using a plate reader. Samples positive for $VEGF_{165}$, but negative for $VEGF_{165}$b were selected for. To purify and concentrate the monoclonal antibodies, the selected clones of hybridoma cells were cultured in DMEM (Sigma Chemical Co., USA) containing 10% bovine IgG-depleted FCS (Hyclone, USA) with 100 units penicillin, 100 μg streptomycin and 2 mM L-glutamine. Monoclonal antibodies were purified on protein-G Sepharose 4 Fast Flow columns (Amersham Biosciences, USA). The antibodies were concentrated with vivaspin 20 (Vivascience AG, Hannover, Germany) and finally dissolved in PBS.

An ELISA assay was used to test each monoclonal antibody clone using the following protocol:
Antigen Coating—for Both 6 Amino Acids and 9 Amino Acids Peptides:
1. $VEGF_{165}$ Free peptide: 10 mg/ml (stock concentration), working concentration 10 μg/ml.
2. $VEGF_{165}$-BSA peptide: 5 mg/ml (stock concentration), working concentration 10 μg/ml.
3. $VEGF_{165}$b (negative control): BSA+peptide, stock concentration, 1 mg/ml; working concentration, 1 ug/ml (1:1,000) in carbonate coating solution
4. $VEGF_{165}$b 6 amino acids-BSA, stock conc., 2.5 mg/ml; working conc., 1 ug/ml (1:2,500 dilution)
5. Peptide-myc (myelocytomatosis viral oncogene homolog): (negative control) myc-BSA, stock conc, 1.4 mg/ml; working conc, 1 ug/ml (1:1,400) in carbonate coating solution.
75 μl/well are added and left for 15 min at 37° C. with shaking or for 1 hr.
The wells are washed 3 times with PBS/Tween.
Cell Supernatant Addition (Samples Supposedly Including Monoclonal Antibody):
75 μl (from 24 well plates), or 75 μl of diluted samples (from 96 well plates) are added in PBS/Tween (as peptides are clean, blocking with BSA is not necessary).
The wells are incubated for 15 min at 37° C. with shaking.
Secondary Antibody Addition:
1:2,500 dilution of HRP-conjugated goat anti-mouse immunoglobulin (Sigma A 0412) were used for peptide detection for less background). Incubation for 15 min at 37° C. with shaking.
Wash 3 times with PBS/Tween
Substrate Addition:
Citrate phosphate buffer, pH 5.0 was warmed to room temperature 30 mg OPD (Sigma, No.-8412) were dissolved in 30 ml of the citrate phosphate buffer, 15 μl of $H_2O_2$ added just prior to use and incubation at room temperature for 15 minutes.
Stopping:
Stopping solution: 100 ul/well of 1 M HCl (40 ml of concentrated HCl was added into a bottle containing 424 ml of $dH_2O$), were added.
Analysis:
Absorbency at 492 nm was measured using a plate reader.

Example 6

Migration Assay for Determining the Potency of Monoclonal Antibody Specific to Agonist VEGF For determining the potency of monoclonal antibodies against pro-angiogenic forms of VEGF a migration inhibition assay using ECV304 endothelial cells was used. The assay determines the ability of the antibody to inhibit migration of ECV304 endothelial cells in response to stimulation with $VEGF_{165}$ and/or $VEGF_{165}b$ and is preformed as following:

ECV304 endothelial cells are starved for 15 to 16 hrs in serum free medium.

8 μm inserts are coated with 200 μl attachment factor and left overnight at 4° C. or >1 h at 37° C. The solution is removed and the inserts are left to air dry in the cell culture hood.

Cells are washed twice in PBS and trypsinised for 5 min (making sure all cells have detached by carefully flicking flask towards inside of hand).

Cells are spin down and resuspend in small known volume of medium+0.1% FCS.

Cells are counted and diluted to 100,000 cells in 500 μl (200,000 cells/ml).

A chemoattractant solution (500 μl/well) is prepared.

Conditions (1 nM is 40 ng/ml $VEGF_{165}$):
1. Positive Control (5% FCS ie regular full media)
2. Negative Control (0.1% FCS ie Low serum)
3. 0 nM antibody+1 nM $VEGF_{165}$
4. 10 nM antibody+1 nM $VEGF_{165}$
5. 20 nM antibody+1 nM $VEGF_{165}$
6. 40 nM antibody+1 nM $VEGF_{165}$
7. 60 nM antibody+1 nM $VEGF_{165}$
8. 80 nM antibody+1 nM $VEGF_{165}$ Solutions should be sterile or filtered sterile.

24 well plates (plates for suspension Greiner, 662102 for suspension growth and not tissue plastic) are used, 500 μl of chemoattractant solution (attachment factor Cascade biologics, s-006-100), are added into the bottom of the well.

Inserts (Millicell-PCF, PI8PO1250) are air-dried and 500 μl of cell suspension is added into the well. Insert are carefully placed into the well without causing bubbles under the insert.

The plates are incubated in incubator for 6 hrs to allow for migration.

Medium is removed from both layers and top and bottom are washed twice with PBS.

300 UL 4% paraformaldehyde/PBS are added to each well and the wells are left for 15 minutes.

The media is aspirated off and wells are washed three times with PBS.

200 UL Hoecst stain (5UG/ml, dilute stock 1:20 in PBS/T) is added to each well and the wells are left in dark for 30-45 min. The wells are washed three times with 0.5% PBS/triton and twice with PBS and non-migrated cells are removed with cotton bud.

The membrane is carefully cut out using a scalpel blade and the membranes are mounted onto slides using Vectashield liquid mount (Vectashield Vector, H-1000), and sealed with nail varnish.

Migrated cells are counted using 40× magnification in 10 random fields at least two fields of view away from the insert edge to account for accumulation of any non-migrated and/or unremoved cells around the insert edge.

For basal/control 15-30 cells per field are counted, for $VEGF_{165}$ 40 ng/ml 80-150 (4-5 fold compared to control). $VEGF_{165}b$ 40 ng/ml on its own gives about 1.5-2 fold increase and $VEGF_{165}+_{165}b$ reduces migration to about 3 fold.

For millipore inserts % migration calculation is:

$$[(\#cell\ counts\ per\ insert/0.0028637)/1\times10^5]*100$$

0.0028637=area of insert occupied by field of view for a 5 mm diameter Millipore insert for Falcon, this value is 0.00477.

Figure 6:
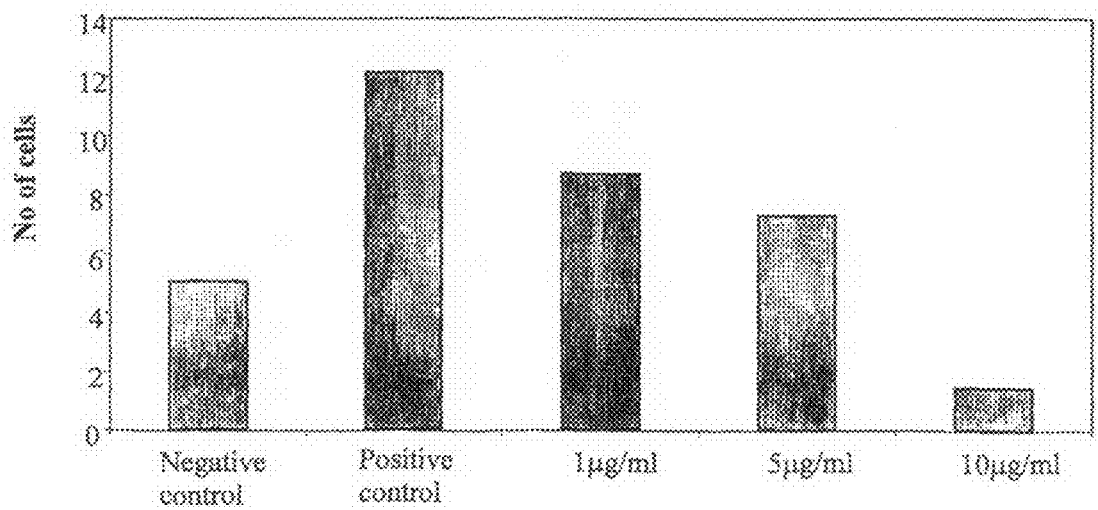
FIG. 6 shows that monoclonal antibodies raised against exon 8a of VEGF inhibit migration of ECV304 endothelial cells in response to stimulation with $VEGF_{165}$.
Figure 7:
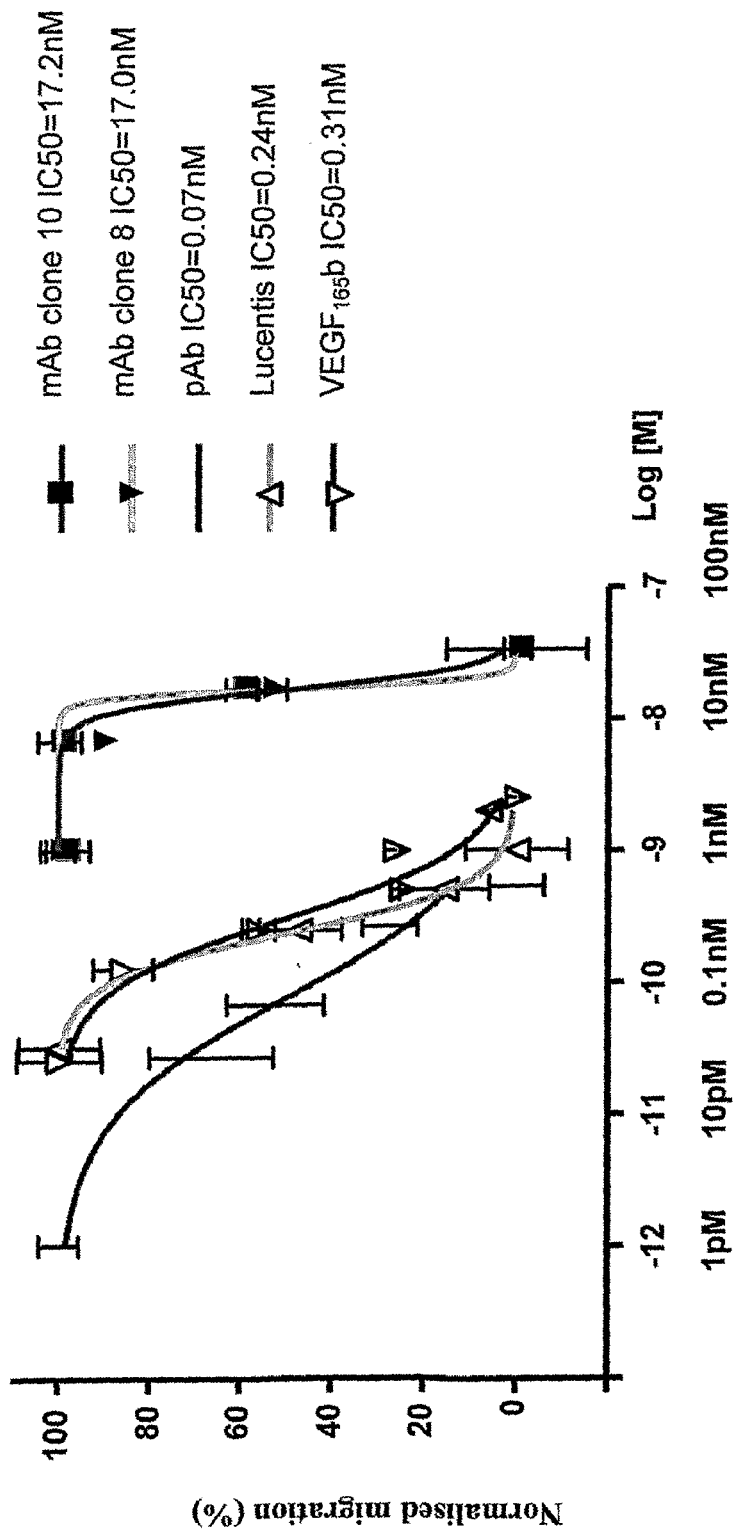
FIG. 7 describes the results of endothelial cell migration assay testing monoclonal and polyclonal antibodies against the agonistic VEGF isform $VEGF_{165}$.

As shown in FIG. 6 the monoclonal antibody raised against exon 8a of $VEGF_{165}$ inhibits migration in a dose dependent manner. FIG. 7 describes the results of endothelial cell migration assay testing monoclonal and polyclonal antibodies against the agonistic VEGF isoform $VEGF_{165}$.

Example 7

Characterization of Anti-VEGFxxx Safety Pharmacology Profile

Antibodies against pro angiogenic VEGF isoforms (VEGFxxx) are tested alone and in combination with $VEGF_{165}b$. The safety profile of the VEGFxxx specific antibodies in animals and humans is expected to be better than the one seen with VEGF scavengers and VEGFR blockers.

VEGF is known to act as a pleiotropic factor. It not only regulates angiogenesis but also serves as a survival factor for many cells and tissue in the body such as neurons, retinal pigmented cells, podocytes in the kidney normal and mature blood vessels. A completed depletion of VEGF such as the one that is achieved by antibodies that do not distinguish between the pro and anti angiogenic forms of VEGF and VEGFR blockers might expose patients to retinal damage, bleeding and proteinuria and kidney impairment and additional serious adverse events.

Antibodies specifically targeted against the pro-angiogenic form of VEGF are expected to be safer and more efficacious since they scavenge the proangiogenic form of VEGF and spare the anti angiogenic forms. This allows the anti-angiogenic form of VEGF to bind the VEGFR1 and VEGFR2 and exert anti-angiogenesis and cell protection. The safety profile of the antibodies specific to pro-angiogenic VEGF isoforms is characterized in several assays:

Cardiovascular Safety Profile

The cardiovascular safety profile of antibodies against the pro-angiogenic form of VEGF is characterize by blood pressure measurements of animal treated with anti-VEGFxxx or VEGF165b or VEGF165 or VEGFR tyrosine kinase inhibitors (TKIs). While the currently available therapies approaches increase blood pressure, antibodies specific to pro-angiogenic VEGF isoforms are expected to have a better safety cardiovascular profile in animals and humans.

Serious side effects of VEGF inhibitors include significant proteinuria. It is shown that $VEGF_{165}b$ does not induce proteinuria, and therefore antibodies specific to the pro-angiogenic forms of VEGF have a better renal safety profile than the one seen with the drugs mentioned above. The effect of antibodies specific to pro-angiogenic isoforms of VEGF is checked by glomerular endothelial cell permeability assays in vitro and in vivo. Antibodies specific to the pro-angiogenic forms of VEGF inhibit permeability induced by $VEGF_{165}$ in glomerular endothelial cells.

Blood pressure measurements are performed in comparison to anti-VEGF antibodies and VEGFR TKIs. While the currently available therapies increase blood pressure, antibodies specific to pro-angiogenic VEGF isoforms are expected to have a better safety cardiovascular profile.

Cytotoxicity Assay on Endothelial Cells

VEGF inhibitors have been shown to cause capillary regression and endothelial cell death. $VEGF_{165}b$ is not cytotoxic, but in contrast is cytoprotective for endothelial cells in culture while VEGF$_{165}$b antibodies increase cytotoxicity. The effect of antibodies specific to the pro-angiogenic forms of VEGF on cell survival is characterized in comparison of VEGF$_{165}$b, VEGF$_{165}$, VEGF scavengers and VEGFR blockers.

Cytotoxicity Assay on Retinal Pigmented Epithelial Cells

VEGF$_{165}$b being a cytoprotective factor is a potential retinal ocular therapeutic. To determine whether VEGF$_{165}$b was toxic or protective for retinal pigmented epithelial cells RPE cells were serum starved and treated with VEGF$_{165}$b or antibodies to VEGF$_{165}$b and cell cytoctoxicity was measured by LDH assays. The results clearly indicate that VEGF$_{165}$b is an endogenous survival factor for RPE cells. Antibodies specific to the pro-angiogenic forms of VEGF are tested for inhibition of retinal pigmented epithelial_cell death induced by serum depletion.

Cytotoxicity Assay on Neurons In Vitro

VEGF$_{165}$b is also cytoprotective for other cell types. Hippocampal neurons from neonatal rats were previously shown to be rescued from cell death during excitotoxciity with glutamate by VEGF$_{165}$. Treatment of CA1 or CA3 neurons with VEGF$_{165}$b reduced glutamate induced cytotoxicity. To determine whether there were regenerative effects of VEGF$_{165}$b, dorsal root ganglia form adult rats were subjected to VEGF$_{165}$b after dissociation in culture and axon length measured. It was shown that VEGF$_{165}$b treatment increased axon length indicating that VEGF$_{165}$b has a cytoprotective and neuronal regenerative property in vitro.

The cytoprotective effect of treatment with antibodies against pro-angiogenic VEGF isoforms, with and without co-treatment of VEGF$_{165}$b, is tested in the appropriate models in comparison to VEGF scavengers and VEGFR TKI in order to characterize the effect on cytoprotection.

Example 8

Humanized and Human Antibodies

A humanized antibody, typically has a human framework grafted with non human CDRs. Thus, a humanized antibody has one or more amino acid sequence introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Nail. Acad. Sci. USA, 90:2551 (1993); Jakobovits et al., Nature, 362:255-258 (1993); Bruggermann et al., Year in Immuno., 7:33 (1993); and Duchosal et al. Nature 355:258 (1992). Human antibodies can also be derived from phage-display libraries (Hoogenboom et al., J. Mol. Biol., 227:381 (1991); Marks et al., J. Mol. Biol., 222:581-597 (1991); Vaughan et al. Nature Biotech 14:309 (1996)).

Example 9

Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv).

Example 10

Renal Safety Profile

The present invention provides antibodies specific to the proangiogenic isoforms of VEGF while sparing the anti-angiogenic forms of VEGF. Significant proteinuria is associated with the treatment of VEGF scavengers and VEGFR blockers.

Figure 8:
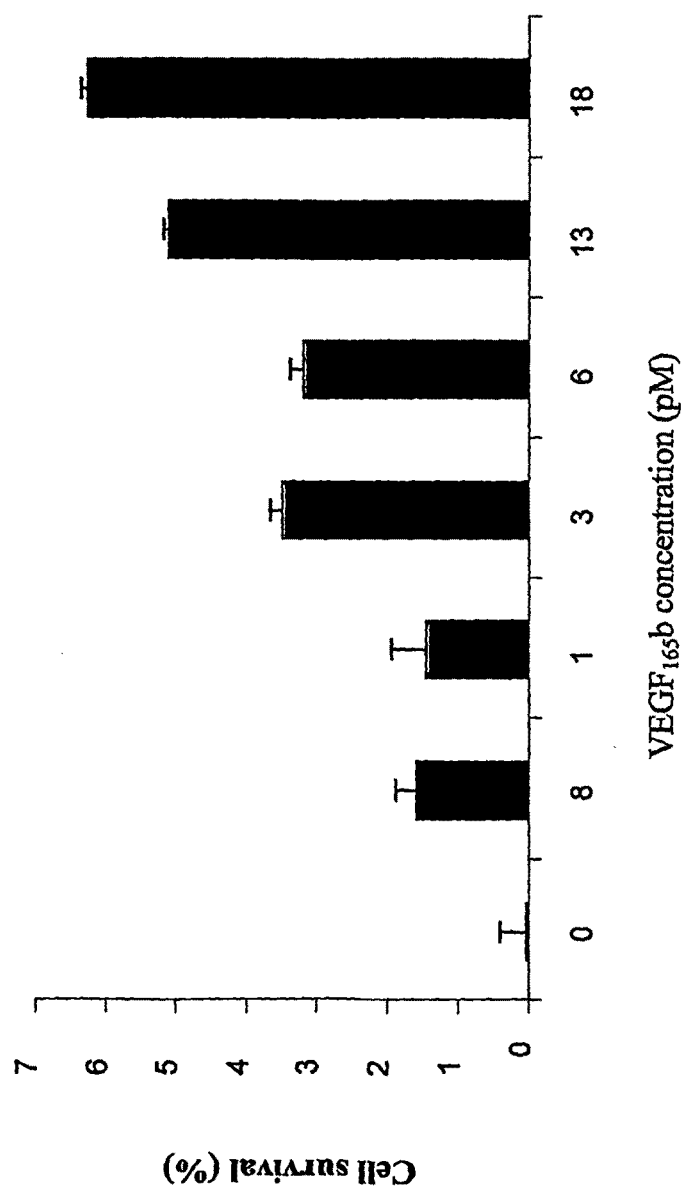
FIG. 8 shows that VEGF165b is a survival factor for serum starved human podocytes.

According to various reports over 30% of AVASTIN treated patients will suffer from proteinuria, which was observed also in preclinical and human clinical trials. Kabbinavar F et al. J Clin Oncol 2003; 21: 60-65; NEJM 2004 350; 2335-2342; Sugimoto H et al J Biol Chem 2003; 278 (15): 12605. This phenomenon is probably because VEGF, as well as being an endothelial survival factor, is an autocrine survival factor for podocytes. Anti-VEGF antibodies increase cell death, while VEGF165 replacement reduces it. It is now disclosed that VEGF165b was found to be a survival factor for serum starved human podocytes as shown is FIG. 8.

As disclosed herein it is now shown that $VEGF_{165}b$ does not induce proteinuria, and it is advantageous that antibodies specific to the pro-angiogenic forms of VEGF will have a better renal safety profile than the one seen with the known drugs, since they can spare the anti angiogenic form.

Figure 9:
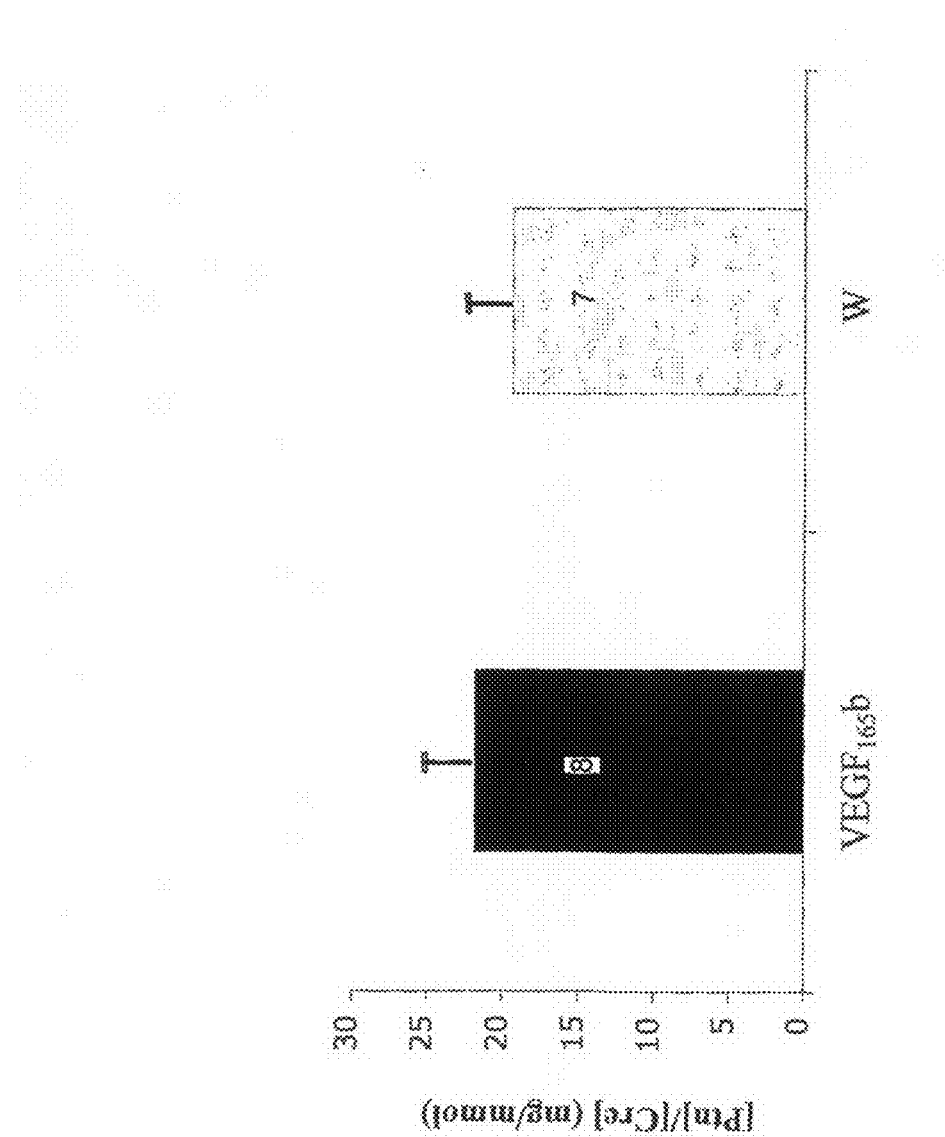
FIG. 9 is a graph depicting urine creatinine/protein ratio from transgenic mice that over-express $VEGF_{165}b$ in the podocytes of the glomerulus after receiving systemic administration of 100 μg of $VEGF_{165}b$.

Renal function, was characterized by the creatinine/protein ratio in urine measured in urine collected from experimental animals. The animals tested included mice bearing human tumors that were treated by systemic administration of 100 ug $VEGF_{165}b$; and transgenic mice that express $VEGF_{165}b$ in the podocytes of the glomerulus (FIG. 9); and rats injected with 1 mg of $VEGF_{165}b$ after measurement of hypertension. In all models that renal function as characterized by the creatinine/protein ratio in urine was found to be normal.

Figure 10:
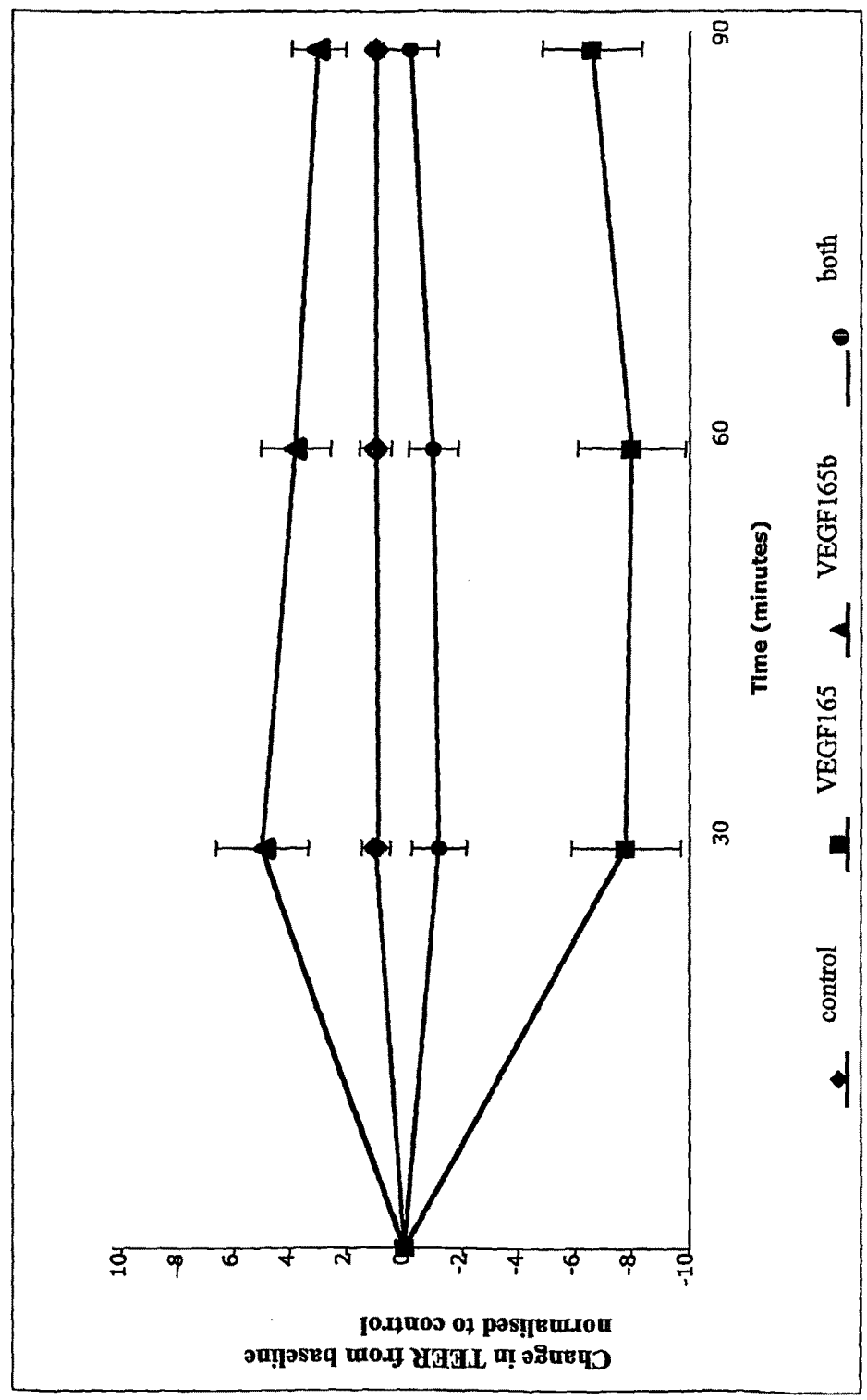
FIG. 10 shows that $VEGF_{165}b$ reduces chronic glomeruli permeability.

Effect on Glomerular Endothelial Cell Permeability In Vitro $VEGF_{165}$ is known to increase vascular permeability and it is through this mechanism that $VEGF_{165}$ expression is thought to maintain a high permeability of the kidney to water, and increase permeability in other tissues. $VEGF_{165}b$ was shown to inhibit the permeability induced by $VEGF_{165}$ in glomerular endothelial cells, when employed a trans-epithelial electrical resistance assay (FIG. 10). Human conditionally immortalized glomerular endothelial cells were serum starved for 2 hours then glomerular trans-endothelial electrical resistance in cultured monolayers was measured in response to either nothing (control), 1 nM VEGF165, 1 nM VEGF165b or a combination of 1 nM VEGF165 & 1 nM VEGF165b. Results are mean fold increase relative to the control (I.e. time point 0 min, SEM). n=5, Data analysis with prism: p±<0.0001, one way ANOVA, repeat measures, with Bonferroni post test. Control vs VEGF165 p<0.001, Control vs VEGF165b p, 0.01, control vs both p>0.05, VEGF165 vs VEGF165b and both p<0.001, VEGF165b vs both p<0.01. Data analysis using SSPS, overall p value >0.0005 one way ANOVA, repeat measures, Post hoc Bonferroni Control vs VEGF 0.001, vs others NSVEGF vs other three groups all significant 165 vs both 0.037. It is favored that antibodies specific to the pro-angiogenic forms of VEGF will also inhibit the permeability induced by $VEGF_{165}$ in glomerular endothelial cells.

Effect on Glomerular Permeability In Vivo $VEGF_{165}$ has been shown to induce proteinuria and increase glomerular permeability in vivo. VEGF antagonists also increase proteinuria and glomerular permeability in vivo. However, in mice expressing $VEGF_{165}b$ for 18 months under the control of the podocyte-specific nephrin promoter, there is a significant reduction in glomerular permeability to water (hydraulic conductivity) (FIG. 11). To determine the effect of continuous treatment of antibodies specific to the pro-angiogenic forms of VEGF in glomeruli in vivo, the permeability of glomeruli isolated from transgenic mice expressing $VEGF_{165}b$ for 18 months, was measured. Glomeruli are isolated from eighteen-month-old wild type, heterozygous, or homozygous pod-$VEGF_{165}b$ mice, and hydraulic conductivity measured per unit area, per unit volume ($L_pA/V_i$). The homozygous mice have a reduced permeability relative to the heterozygote, indicating gene dosage effect. The effect of treatment with antibodies specific to the pro-angiogenic forms of VEGF are similarly tested in comparison to other VEGF scavengers and VEGFR TKI in order to characterize the effect on renal safety profile.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A monoclonal antibody produced by a hybridoma cell line selected from the group consisting of: MR93 A26 clone 13-8-8 Deposit Number 08101401; MR93 A26 clone 13-8-10 Deposit Number 08101402; and MR93 A26 clone 13-8-3 Deposit Number 08101403; deposited with the European Collection of Cell Cultures (ECACC).

2. TheAn isolated antibody or antigen binding fragment thereof specific to pro-angiogenic VEGF, wherein the isolated antibody or the antigen binding fragment thereof binds to an epitope consisting of the amino acid sequence RCDKPRR (SEQ ID NO:3).

3. An isolated antibody or antigen binding fragment thereof specific to pro-angiogenic VEGF, wherein the isolated antibody or the antigen binding fragment thereof binds to an epitope consisting of the amino acid sequence CRCDKPRR (SEQ ID NO:4).

4. An isolated antibody or antigen binding fragment thereof specific to pro-angiogenic VEGF, wherein the isolated antibody or the antigen binding fragment thereof binds to an epitope consisting of the amino acid sequence TCRCDKPRR (SEQ ID NO:5).

* * * * *

UNITED STATES PATENT AND TRADEMARK OFFICE
CERTIFICATE OF CORRECTION

PATENT NO. : 8,592,563 B2 Page 1 of 1
APPLICATION NO. : 12/739619
DATED : November 26, 2013
INVENTOR(S) : Bates et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 28 days.

Signed and Sealed this
Twenty-second Day of September, 2015

Michelle K. Lee
*Director of the United States Patent and Trademark Office*